United States Patent
Lopez et al.

(10) Patent No.: US 11,319,516 B2
(45) Date of Patent: May 3, 2022

(54) USE OF CYSTEINE ENDOPROTEASE FOR REDUCING CLOUDINESS IN DRINKS

(71) Applicants: MALTERIES SOUFFLET, Nogent sur Seine (FR); INSTITUT NATIONAL DE LA RECHERCHE AGRONOMIQUE (INRA), Paris (FR)

(72) Inventors: Michel Lopez, Sains en Amienois (FR); Myriam Fliss, La Motte Tilly (FR); Didier Gilbert Marion, Nantes (FR)

(73) Assignees: MALTERIES SOUFFLET, Nogent sur Seine (FR); INSTITUT NATIONAL DE RECHERCHE POUR L'AGRICULTURE. L'ALIMENTATION ET L'ENVIRONNEMENT, Paris (FR)

( * ) Notice: Subject to any disclaimer, the term of this patent is extended or adjusted under 35 U.S.C. 154(b) by 643 days.

(21) Appl. No.: 15/570,074

(22) PCT Filed: Apr. 29, 2016

(86) PCT No.: PCT/EP2016/059691
§ 371 (c)(1),
(2) Date: Oct. 27, 2017

(87) PCT Pub. No.: WO2016/174244
PCT Pub. Date: Nov. 3, 2016

(65) Prior Publication Data
US 2018/0112158 A1    Apr. 26, 2018

(30) Foreign Application Priority Data
Apr. 29, 2015 (FR) ...................................... 15 53869

(51) Int. Cl.
| | | |
|---|---|---|
| C12C 5/00 | (2006.01) | |
| C12C 1/18 | (2006.01) | |
| C12C 11/00 | (2006.01) | |
| C12N 9/64 | (2006.01) | |
| A23L 2/84 | (2006.01) | |

(52) U.S. Cl.
CPC ................ *C12C 5/004* (2013.01); *A23L 2/84* (2013.01); *C12C 1/18* (2013.01); *C12C 11/003* (2013.01); *C12N 9/6472* (2013.01); *C12Y 304/22* (2013.01)

(58) Field of Classification Search
CPC .......... C12C 5/004; C12C 11/003; C12C 1/18; A23L 2/84; C12N 9/6472; C12Y 304/22
USPC ..................................... 426/11, 16, 592, 590
See application file for complete search history.

(56) References Cited

U.S. PATENT DOCUMENTS

| | | |
|---|---|---|
| 8,257,760 B2 | 9/2012 | Edens et al. |
| 8,524,225 B2 | 9/2013 | Edens et al. |
| 8,778,338 B2 | 7/2014 | Gass et al. |
| 2004/0115306 A1 | 6/2004 | Lopez |
| 2010/0092451 A1 | 4/2010 | Gass et al. |
| 2012/0141628 A1 | 6/2012 | Lopez et al. |
| 2015/0307823 A1 | 10/2015 | Mutsaers et al. |

FOREIGN PATENT DOCUMENTS

WO    WO-2014191298    12/2014

OTHER PUBLICATIONS

Berne L. Jones et al How various malt endoproteinase classes affect wort soluble protein levels USDA, ARS, Cereal Crops Research Unit, 501 N. Walnut Street, Madison, WI 53726, USA Received May 7, 2004; revised Sep. 12, 2004; accepted Sep. 13, 2004 https://naldc.nal.usda.gov/download/7676/PDF (Year: 2004).*
International Search Report for PCT/EP2016/059691, dated Jul. 20, 2016.
Written Opinion for PCT/EP2016/059691, dated Jul. 20, 2016.
Preliminary Search Report for FR 1553869, dated Feb. 15, 2015.
Nelson, et al, "The Addition of Proteases to the Fermenter to Control Chill-Haze Formation", Mar.-Apr. 1987, pp. 116-120, vol. 93, J. Inst. Brew.
Lopez, et al, "Effective Prevention of Chill-Haze in Beer Using an Acid Proline-Specific Endoprotease for Aspergillus niger",2005, pp. 7944-7949, vol. 53, J. Agric .Food Chem.

* cited by examiner

*Primary Examiner* — Vera Stulii
(74) *Attorney, Agent, or Firm* — B. Aaron Schulman, Esq.; Stites & Harbison, PLLC

(57) ABSTRACT

The present invention relates to the use of a cysteine endoprotease or a malt extract to prevent or reduce the cloudiness of a cereal-based beverage, fermented or not.

38 Claims, 12 Drawing Sheets
Specification includes a Sequence Listing.

SEQUENCE LISTING

```
<160> NUMBER OF SEQ ID NOS: 8

<210> SEQ ID NO 1
<211> LENGTH: 365
<212> TYPE: PRT
<213> ORGANISM: Hordeum vulgare

<400> SEQUENCE: 1

Met Trp Arg Cys Ile Leu Leu Ser Ala Val Val Val Ala Leu Ala Leu
1               5                   10                  15

Ala Pro Ala Pro Ala Leu Gly Val Pro Phe Thr Glu Lys Asp Leu Ala
            20                  25                  30
```

```
Ser Glu Glu Ser Leu Arg Gly Leu Tyr Glu Arg Trp Arg Ser His Tyr
            35                  40                  45

Thr Val Ser Arg Arg Gly Leu Gly Ala Asp Ala Glu Glu Arg Arg Phe
    50                  55                  60

Asn Val Phe Lys Glu Asn Ala Arg Tyr Val His Glu Gly Asn Lys Arg
65                  70                  75                  80

Asp Arg Pro Phe Arg Leu Ala Leu Asn Lys Phe Ala Asp Met Thr Thr
                85                  90                  95

Asp Glu Phe Arg Arg Thr Tyr Ala Gly Ser Arg Val Arg His His Leu
            100                 105                 110

Ser Leu Ser Gly Gly Arg Arg Gly Asp Gly Gly Phe Arg Tyr Ala Asp
        115                 120                 125

Ala Asp Asn Leu Pro Pro Ala Val Asp Trp Arg Gln Lys Gly Ala Val
130                 135                 140

Thr Ala Ile Lys Asp Gln Gly Gln Cys Gly Ser Cys Trp Ala Phe Ser
145                 150                 155                 160

Thr Ile Val Ala Val Glu Gly Ile Asn Lys Ile Arg Thr Gly Lys Leu
                165                 170                 175

Val Ser Leu Ser Glu Gln Glu Leu Met Asp Cys Asp Asn Val Asn Asn
            180                 185                 190

Gln Gly Cys Glu Gly Gly Leu Met Asp Tyr Ala Phe Gln Phe Ile Gln
        195                 200                 205

Lys Asn Gly Ile Thr Thr Glu Ser Asn Tyr Pro Tyr Gln Gly Glu Gln
210                 215                 220

Gly Ser Cys Asp Gln Ala Lys Glu Asn Ala Gln Ala Val Thr Ile Asp
225                 230                 235                 240

Gly Tyr Glu Asp Val Pro Ala Asn Asp Glu Ser Ala Leu Gln Lys Ala
                245                 250                 255

Val Ala Gly Gln Pro Val Ser Val Ala Ile Asp Ala Ser Gly Gln Asp
            260                 265                 270

Phe Gln Phe Tyr Ser Glu Gly Val Phe Thr Gly Glu Cys Ser Thr Asp
        275                 280                 285

Leu Asp His Gly Val Ala Ala Val Gly Tyr Gly Ala Thr Arg Asp Gly
290                 295                 300

Thr Lys Tyr Trp Ile Val Lys Asn Ser Trp Gly Glu Asp Trp Gly Glu
305                 310                 315                 320

Lys Gly Tyr Ile Arg Met Gln Arg Gly Val Ser Gln Thr Glu Gly Leu
                325                 330                 335

Cys Gly Ile Ala Met Gln Ala Ser Tyr Pro Thr Lys Ser Ala Pro His
            340                 345                 350

Ala Ser Thr Val Arg Glu Gly Ser His Thr Asp Glu Leu
        355                 360                 365

<210> SEQ ID NO 2
<211> LENGTH: 365
<212> TYPE: PRT
<213> ORGANISM: Hordeum vulgare

<400> SEQUENCE: 2

Met Trp Arg Cys Ile Leu Leu Ser Ala Val Val Ala Leu Ala Leu
1               5                   10                  15

Ala Pro Ala Pro Ala Leu Gly Val Pro Phe Thr Glu Lys Asp Leu Ala
            20                  25                  30

Ser Glu Glu Ser Leu Arg Gly Leu Tyr Glu Arg Trp Arg Ser His Tyr
        35                  40                  45
```

```
Thr Val Ser Arg Arg Gly Leu Gly Ala Asp Ala Glu Glu Arg Arg Phe
            50                  55                  60

Asn Val Phe Lys Gln Asn Ala Arg Tyr Val His Glu Gly Asn Lys Arg
 65                  70                  75                  80

Asp Met Pro Phe Arg Leu Ala Leu Asn Lys Phe Ala Asp Met Thr Thr
                    85                  90                  95

Asp Glu Phe Arg Arg Thr Tyr Ala Gly Ser Arg Val Arg His His Leu
                100                 105                 110

Ser Leu Ser Gly Gly Arg Arg Gly Asp Gly Gly Phe Arg Tyr Gly Asp
            115                 120                 125

Ala Asp Asn Leu Pro Pro Ala Val Asp Trp Arg Gln Lys Gly Ala Val
            130                 135                 140

Thr Ala Ile Lys Asp Gln Gly Gln Cys Gly Ser Cys Trp Ala Phe Ser
145                 150                 155                 160

Thr Ile Val Ala Val Glu Gly Ile Asn Lys Ile Arg Thr Gly Lys Leu
                165                 170                 175

Val Ser Leu Ser Glu Gln Glu Leu Met Asp Cys Asp Asn Val Asn Asn
                180                 185                 190

Gln Gly Cys Asp Gly Gly Leu Met Asp Tyr Ala Phe Gln Phe Ile Gln
            195                 200                 205

Lys Asn Gly Ile Thr Thr Glu Ser Asn Tyr Pro Tyr Gln Gly Glu Gln
210                 215                 220

Gly Ser Cys Asp Gln Ala Lys Glu Asn Ala Gln Ala Val Thr Ile Asp
225                 230                 235                 240

Gly Tyr Glu Asp Val Pro Ala Asn Asp Glu Ser Ala Leu Gln Lys Ala
                245                 250                 255

Val Ala Gly Gln Pro Val Ser Val Ala Ile Asp Ala Ser Gly Gln Asp
                260                 265                 270

Phe Gln Phe Tyr Ser Glu Gly Val Phe Thr Gly Glu Cys Ser Thr Asp
            275                 280                 285

Leu Asp His Gly Val Ala Ala Val Gly Tyr Gly Ala Thr Arg Asp Gly
            290                 295                 300

Thr Lys Tyr Trp Ile Val Lys Asn Ser Trp Gly Glu Asp Trp Gly Glu
305                 310                 315                 320

Lys Gly Tyr Ile Arg Met Gln Arg Gly Val Ser Gln Thr Glu Gly Leu
                325                 330                 335

Cys Gly Ile Ala Met Gln Ala Ser Tyr Pro Thr Lys Ser Ala Pro His
            340                 345                 350

Ala Ser Thr Val Arg Glu Glu Ser His Thr Asp Glu Leu
            355                 360                 365

<210> SEQ ID NO 3
<211> LENGTH: 371
<212> TYPE: PRT
<213> ORGANISM: Hordeum vulgare

<400> SEQUENCE: 3

Met Gly Leu Leu Ser Lys Lys Leu Leu Val Ala Ser Met Val Ala Ala
 1               5                  10                  15

Val Leu Ala Val Ala Ala Val Glu Leu Cys Ser Ala Ile Pro Met Glu
                20                  25                  30

Asp Lys Asp Leu Glu Ser Glu Glu Ala Leu Trp Asp Leu Tyr Glu Arg
                35                  40                  45

Trp Gln Ser Ala His Arg Val Arg Arg His His Ala Glu Lys His Arg
```

```
            50                  55                  60
Arg Phe Gly Thr Phe Lys Ser Asn Ala His Phe Ile His Ser His Asn
 65                  70                  75                  80

Lys Arg Gly Asp His Pro Tyr Arg Leu His Leu Asn Arg Phe Gly Asp
                 85                  90                  95

Met Asp Gln Ala Glu Phe Arg Ala Thr Phe Val Gly Asp Leu Arg Arg
            100                 105                 110

Asp Thr Pro Ala Lys Pro Ser Val Pro Gly Phe Met Tyr Ala Ala
            115                 120                 125

Leu Asn Val Ser Asp Leu Pro Pro Ser Val Asp Trp Arg Gln Lys Gly
130                 135                 140

Ala Val Thr Gly Val Lys Asp Gln Gly Lys Cys Gly Ser Cys Trp Ala
145                 150                 155                 160

Phe Ser Thr Val Val Ser Val Glu Gly Ile Asn Ala Ile Arg Thr Gly
                165                 170                 175

Ser Leu Val Ser Leu Ser Glu Gln Glu Leu Ile Asp Cys Asp Thr Ala
            180                 185                 190

Asp Asn Asp Gly Cys Gln Gly Gly Leu Met Asp Asn Ala Phe Glu Tyr
            195                 200                 205

Ile Lys Asn Asn Gly Gly Leu Ile Thr Glu Ala Ala Tyr Pro Tyr Arg
210                 215                 220

Ala Ala Arg Gly Thr Cys Asn Val Ala Arg Ala Ala Gln Asn Ser Pro
225                 230                 235                 240

Val Val Val His Ile Asp Gly His Gln Asp Val Pro Ala Asn Ser Glu
                245                 250                 255

Glu Asp Leu Ala Arg Ala Val Ala Asn Gln Pro Val Ser Val Ala Val
            260                 265                 270

Glu Ala Ser Gly Lys Ala Phe Met Phe Tyr Ser Glu Gly Val Phe Thr
            275                 280                 285

Gly Asp Cys Gly Thr Glu Leu Asp His Gly Val Ala Val Val Gly Tyr
            290                 295                 300

Gly Val Ala Glu Asp Gly Lys Ala Tyr Trp Thr Val Lys Asn Ser Trp
305                 310                 315                 320

Gly Pro Ser Trp Gly Glu Gln Gly Tyr Ile Arg Val Glu Lys Asp Ser
                325                 330                 335

Gly Ala Ser Gly Gly Leu Cys Gly Ile Ala Met Glu Ala Ser Tyr Pro
            340                 345                 350

Val Lys Thr Tyr Asn Lys Pro Met Pro Arg Arg Ala Leu Gly Ala Trp
            355                 360                 365

Glu Ser Gln
370

<210> SEQ ID NO 4
<211> LENGTH: 373
<212> TYPE: PRT
<213> ORGANISM: Hordeum vulgare

<400> SEQUENCE: 4

Met Gly Leu Leu Ser Lys Lys Leu Leu Val Ala Ser Met Val Ala Ala
 1               5                  10                  15

Val Leu Ala Val Ala Ala Val Glu Leu Cys Ser Ala Ile Pro Met Glu
                20                  25                  30

Asp Lys Asp Leu Glu Ser Glu Glu Ala Leu Trp Asp Leu Tyr Glu Arg
            35                  40                  45
```

```
Trp Gln Ser Ala His Arg Val Arg Arg His His Ala Glu Lys His Arg
         50                  55                  60
Arg Phe Gly Thr Phe Lys Ser Asn Ala His Phe Ile His Ser His Asn
 65                  70                  75                  80
Lys Arg Gly Asp His Pro Tyr Arg Leu His Leu Asn Arg Phe Gly Asp
                 85                  90                  95
Met Asp Gln Ala Glu Phe Arg Ala Thr Phe Val Gly Asp Leu Arg Arg
                100                 105                 110
Asp Thr Pro Ser Lys Pro Pro Ser Val Pro Gly Phe Met Tyr Ala Ala
                115                 120                 125
Leu Asn Val Ser Asp Leu Pro Pro Ser Val Asp Trp Arg Gln Lys Gly
        130                 135                 140
Ala Val Thr Gly Val Lys Asp Gln Gly Lys Cys Gly Ser Cys Trp Ala
145                 150                 155                 160
Phe Ser Thr Val Val Ser Val Glu Gly Ile Asn Ala Ile Arg Thr Gly
                165                 170                 175
Ser Leu Val Ser Leu Ser Glu Gln Glu Leu Ile Asp Cys Asp Thr Ala
        180                 185                 190
Asp Asn Asp Gly Cys Gln Gly Gly Leu Met Asp Asn Ala Phe Glu Tyr
        195                 200                 205
Ile Lys Asn Asn Gly Gly Leu Ile Thr Glu Ala Ala Tyr Pro Tyr Arg
        210                 215                 220
Ala Ala Arg Gly Thr Cys Asn Val Ala Arg Ala Ala Gln Asn Ser Pro
225                 230                 235                 240
Val Val Val His Ile Asp Gly His Gln Asp Val Pro Ala Asn Ser Glu
                245                 250                 255
Glu Asp Leu Ala Arg Ala Val Ala Asn Gln Pro Val Ser Val Ala Val
                260                 265                 270
Glu Ala Ser Gly Lys Ala Phe Met Phe Tyr Ser Glu Gly Val Phe Thr
        275                 280                 285
Gly Glu Cys Gly Thr Glu Leu Asp His Gly Val Ala Val Val Gly Tyr
        290                 295                 300
Gly Val Ala Glu Asp Gly Lys Ala Tyr Trp Thr Val Lys Asn Ser Trp
305                 310                 315                 320
Gly Pro Ser Trp Gly Glu Gln Gly Tyr Ile Arg Val Glu Lys Asp Ser
                325                 330                 335
Gly Ala Ser Gly Gly Leu Cys Gly Ile Ala Met Glu Ala Ser Tyr Pro
                340                 345                 350
Val Lys Thr Tyr Ser Lys Pro Lys Pro Thr Pro Arg Arg Ala Leu Gly
        355                 360                 365
Ala Arg Glu Ser Leu
    370

<210> SEQ ID NO 5
<211> LENGTH: 238
<212> TYPE: PRT
<213> ORGANISM: Hordeum vulgare

<400> SEQUENCE: 5

Asp Ala Asp Asn Leu Pro Pro Val Asp Trp Arg Gln Lys Gly Ala
 1               5                  10                  15

Val Thr Ala Ile Lys Asp Gln Gly Gln Cys Gly Ser Cys Trp Ala Phe
                 20                  25                  30

Ser Thr Ile Val Ala Val Glu Gly Ile Asn Lys Ile Arg Thr Gly Lys
         35                  40                  45
```

```
Leu Val Ser Leu Ser Glu Gln Glu Leu Met Asp Cys Asp Asn Val Asn
    50                  55                  60

Asn Gln Gly Cys Glu Gly Gly Leu Met Asp Tyr Ala Phe Gln Phe Ile
 65                 70                  75                  80

Gln Lys Asn Gly Ile Thr Thr Glu Ser Asn Tyr Pro Tyr Gln Gly Glu
                 85                  90                  95

Gln Gly Ser Cys Asp Gln Ala Lys Glu Asn Ala Gln Ala Val Thr Ile
             100                 105                 110

Asp Gly Tyr Glu Asp Val Pro Ala Asn Asp Glu Ser Ala Leu Gln Lys
         115                 120                 125

Ala Val Ala Gly Gln Pro Val Ser Val Ala Ile Asp Ala Ser Gly Gln
     130                 135                 140

Asp Phe Gln Phe Tyr Ser Glu Gly Val Phe Thr Gly Glu Cys Ser Thr
145                 150                 155                 160

Asp Leu Asp His Gly Val Ala Ala Val Gly Tyr Gly Ala Thr Arg Asp
                165                 170                 175

Gly Thr Lys Tyr Trp Ile Val Lys Asn Ser Trp Gly Glu Asp Trp Gly
                180                 185                 190

Glu Lys Gly Tyr Ile Arg Met Gln Arg Gly Val Ser Gln Thr Glu Gly
            195                 200                 205

Leu Cys Gly Ile Ala Met Gln Ala Ser Tyr Pro Thr Lys Ser Ala Pro
    210                 215                 220

His Ala Ser Thr Val Arg Glu Gly Ser His Thr Asp Glu Leu
225                 230                 235

<210> SEQ ID NO 6
<211> LENGTH: 238
<212> TYPE: PRT
<213> ORGANISM: Hordeum vulgare

<400> SEQUENCE: 6

Asp Ala Asp Asn Leu Pro Pro Ala Val Asp Trp Arg Gln Lys Gly Ala
1               5                   10                  15

Val Thr Ala Ile Lys Asp Gln Gly Gln Cys Gly Ser Cys Trp Ala Phe
            20                  25                  30

Ser Thr Ile Val Ala Val Glu Gly Ile Asn Lys Ile Arg Thr Gly Lys
        35                  40                  45

Leu Val Ser Leu Ser Glu Gln Glu Leu Met Asp Cys Asp Asn Val Asn
    50                  55                  60

Asn Gln Gly Cys Asp Gly Gly Leu Met Asp Tyr Ala Phe Gln Phe Ile
 65                 70                  75                  80

Gln Lys Asn Gly Ile Thr Thr Glu Ser Asn Tyr Pro Tyr Gln Gly Glu
                 85                  90                  95

Gln Gly Ser Cys Asp Gln Ala Lys Glu Asn Ala Gln Ala Val Thr Ile
             100                 105                 110

Asp Gly Tyr Glu Asp Val Pro Ala Asn Asp Glu Ser Ala Leu Gln Lys
         115                 120                 125

Ala Val Ala Gly Gln Pro Val Ser Val Ala Ile Asp Ala Ser Gly Gln
     130                 135                 140

Asp Phe Gln Phe Tyr Ser Glu Gly Val Phe Thr Gly Glu Cys Ser Thr
145                 150                 155                 160

Asp Leu Asp His Gly Val Ala Ala Val Gly Tyr Gly Ala Thr Arg Asp
                165                 170                 175

Gly Thr Lys Tyr Trp Ile Val Lys Asn Ser Trp Gly Glu Asp Trp Gly
```

```
                180                 185                 190
Glu Lys Gly Tyr Ile Arg Met Gln Arg Gly Val Ser Gln Thr Glu Gly
            195                 200                 205

Leu Cys Gly Ile Ala Met Gln Ala Ser Tyr Pro Thr Lys Ser Ala Pro
        210                 215                 220

His Ala Ser Thr Val Arg Glu Glu Ser His Thr Asp Glu Leu
225                 230                 235

<210> SEQ ID NO 7
<211> LENGTH: 241
<212> TYPE: PRT
<213> ORGANISM: Hordeum vulgare

<400> SEQUENCE: 7

Val Ser Asp Leu Pro Pro Ser Val Asp Trp Arg Gln Lys Gly Ala Val
1               5                   10                  15

Thr Gly Val Lys Asp Gln Gly Lys Cys Gly Ser Cys Trp Ala Phe Ser
            20                  25                  30

Thr Val Val Ser Val Glu Gly Ile Asn Ala Ile Arg Thr Gly Ser Leu
        35                  40                  45

Val Ser Leu Ser Glu Gln Glu Leu Ile Asp Cys Asp Thr Ala Asp Asn
    50                  55                  60

Asp Gly Cys Gln Gly Gly Leu Met Asp Asn Ala Phe Glu Tyr Ile Lys
65                  70                  75                  80

Asn Asn Gly Gly Leu Ile Thr Glu Ala Ala Tyr Pro Tyr Arg Ala Ala
                85                  90                  95

Arg Gly Thr Cys Asn Val Ala Arg Ala Ala Gln Asn Ser Pro Val Val
            100                 105                 110

Val His Ile Asp Gly His Gln Asp Val Pro Ala Asn Ser Glu Glu Asp
        115                 120                 125

Leu Ala Arg Ala Val Ala Asn Gln Pro Val Ser Val Ala Val Glu Ala
    130                 135                 140

Ser Gly Lys Ala Phe Met Phe Tyr Ser Glu Gly Val Phe Thr Gly Asp
145                 150                 155                 160

Cys Gly Thr Glu Leu Asp His Gly Val Ala Val Val Gly Tyr Gly Val
                165                 170                 175

Ala Glu Asp Gly Lys Ala Tyr Trp Thr Val Lys Asn Ser Trp Gly Pro
            180                 185                 190

Ser Trp Gly Glu Gln Gly Tyr Ile Arg Val Glu Lys Asp Ser Gly Ala
        195                 200                 205

Ser Gly Gly Leu Cys Gly Ile Ala Met Glu Ala Ser Tyr Pro Val Lys
    210                 215                 220

Thr Tyr Asn Lys Pro Met Pro Arg Arg Ala Leu Gly Ala Trp Glu Ser
225                 230                 235                 240

Gln

<210> SEQ ID NO 8
<211> LENGTH: 243
<212> TYPE: PRT
<213> ORGANISM: Hordeum vulgare

<400> SEQUENCE: 8

Val Ser Asp Leu Pro Pro Ser Val Asp Trp Arg Gln Lys Gly Ala Val
1               5                   10                  15

Thr Gly Val Lys Asp Gln Gly Lys Cys Gly Ser Cys Trp Ala Phe Ser
            20                  25                  30
```

```
Thr Val Val Ser Val Glu Gly Ile Asn Ala Ile Arg Thr Gly Ser Leu
        35                  40                  45
Val Ser Leu Ser Glu Gln Glu Leu Ile Asp Cys Asp Thr Ala Asp Asn
        50                  55                  60
Asp Gly Cys Gln Gly Gly Leu Met Asp Asn Ala Phe Glu Tyr Ile Lys
65                  70                  75                  80
Asn Asn Gly Gly Leu Ile Thr Glu Ala Ala Tyr Pro Tyr Arg Ala Ala
                85                  90                  95
Arg Gly Thr Cys Asn Val Ala Arg Ala Ala Gln Asn Ser Pro Val Val
                100                 105                 110
Val His Ile Asp Gly His Gln Asp Val Pro Ala Asn Ser Glu Glu Asp
        115                 120                 125
Leu Ala Arg Ala Val Ala Asn Gln Pro Val Ser Val Ala Val Glu Ala
        130                 135                 140
Ser Gly Lys Ala Phe Met Phe Tyr Ser Glu Gly Val Phe Thr Gly Glu
145                 150                 155                 160
Cys Gly Thr Glu Leu Asp His Gly Val Ala Val Val Gly Tyr Gly Val
                165                 170                 175
Ala Glu Asp Gly Lys Ala Tyr Trp Thr Val Lys Asn Ser Trp Gly Pro
                180                 185                 190
Ser Trp Gly Glu Gln Gly Tyr Ile Arg Val Glu Lys Asp Ser Gly Ala
        195                 200                 205
Ser Gly Gly Leu Cys Gly Ile Ala Met Glu Ala Ser Tyr Pro Val Lys
        210                 215                 220
Thr Tyr Ser Lys Pro Lys Pro Thr Pro Arg Arg Ala Leu Gly Ala Arg
225                 230                 235                 240
Glu Ser Leu
```

USE OF CYSTEINE ENDOPROTEASE FOR REDUCING CLOUDINESS IN DRINKS

The present invention relates to processes for clarifying beverages, in particular beer.

Clarification is an essential step in the beverage industry, which is confronted with the formation of cloudiness during the storage of beer, wine, or even fruit juices. Being a major problem, numerous studies have been carried out on the subject and it is now a well-known phenomenon. The formation of the colloidal cloudiness is due to polyphenol-protein and protein-protein interactions. The cloudiness depends on the protein-polyphenol ratio present in the wort but also on the proline content of the proteins present in the wort, the degree of polymerization, as well as the number of hydroxyl groups of the polyphenols (Siebert (2006) LWT 39: 987-994).

More specifically, in the case of beer, it has been shown that the proteins involved in the formation of the cloudiness were malt hordeins (Steiner et al., (2011) Eur. Food Res. Technol., 232: 191-204). Most hordeins disappear during the brewing process as they are hydrolysed by the endogenous proteases of the malt. Analysis of the proteins constituting the beer, however, showed the presence of residual B and γ3 hordeins (Perrocheau et al., 2005) Proteomics 5: 2849-2858, Jin et al., (2011) J. Food Biochem. 35:1522-1527), which are responsible for the formation of the cloudiness.

In order to stabilize the beer, many alternatives have been implemented by brewers to eliminate the compounds involved in the cloudiness. Physical means may be used such as the removal of proteins by bentonite, but this interaction is aspecific and eliminates the proteins involved in the formation of the cloudiness as well as those of the foam. The same disadvantages are associated with the use of ultrafiltration.

It has also been proposed to add proline-rich proteins such as gelatin, or polyphenols such as tannic acid, to the beverage prior to storage, in order to promote precipitation and elimination of the substance at the origin of the formation of the cloudiness. Another alternative is to use silica gels that bind proline-rich proteins more specifically. These silica gels however are rather ineffective in clarifying beverages rich in polyphenols. Polyvinylpolypyrrolidone (PVPP) is often used to extract the polyphenol fraction. However, polyphenols have an antioxidant role that may be beneficial. The filtration after a low temperature passage inducing the formation of the cloudiness, is also used, but the latter technique has the disadvantage of taking a long time (several months).

Enzymatic means are also used such as the hydrolysis of the protein fraction by a very wide-action specific natural protease, papain, but the latter also degrades the proteins of the foam, which is an undesirable side effect. More recently, the use of a proline-specific endoprotease specifically degrading prolamins has been described: Brewers Clarex® which is a recombinant prolyl-endoprotease of class EC 3.4.21.26 derived from a filamentous fungus: *Aspergillus niger* (U.S. Pat. No. 8,119,171). Nevertheless, this endoprotease may also degrade the proteins of the foam.

There is, therefore, still a significant need for effective alternative means to reduce the cloudiness of beverages, in particular low-cost means, which do not require significant modification of the beverage manufacturing equipment, and which do not have the disadvantages of the known prior art techniques, in particular having no impact on the foam.

During germination, cereal grains produce proteases which hydrolyze the reserve proteins to ensure the development of the seedling. The presence of at least about forty proteases in green malt has been reported by Zhang and Jones (1995) J. Cereal Sci. 21:145-153. These proteases belong to the four existing types: serine, metallo, cysteine and aspartyl-proteases. However, it has been demonstrated that the proteases mainly responsible for the degradation of prolamins during the germination of the grains are cysteine proteases (Shi and Xu (2009) J. Integrative Plant Biol., 51: 52-57). Because of the activity of these proteases on prolamins, it has been proposed to use them to decrease the peptide content inducing the celiac immune response in cereal products, or during the digestion of these food products (Stenman et al. al., (2010) Clin. Immunol. 161: 242-249). The addition of recombinant barley EP-B protease has recently been proposed as a feed additive in pig feed, to increase the digestibility of insoluble barley proteins (Christensen et al., (2014) J. Agric. Food Chem. 62: 8562-8570). To the inventors' knowledge, none of these potential applications has been implemented and no other application of these cysteine endoproteases has been suggested so far.

The present invention results from the unexpected discovery by the inventors that malt, in particular malt extract, contains protease activity capable of effectively decreasing beer cloudiness. The inventors have more particularly demonstrated that this protease activity involves cysteine endoproteases, and, more particularly, endoproteases A and B in barley malt.

The utility of endoproteases A and B of barley is all the more surprising in that, unlike many proteases, the presence of proline, an amino acid widely present in hordeins, does not appear to penalize their proteolytic activity. Cereal cysteine endoproteases are capable of cleaving the N-terminal repeat domains of proline and glutamine-rich hordeins and gliadins (Bethune et al., (2006) Chem. Biol. 13: 637-647).

Furthermore, the inventors have demonstrated that this proteasic activity allows, in parallel and in a surprising manner, an increase in the fermentation yield during the manufacture of the beer.

The present invention therefore relates to the use of at least one cysteine endoprotease comprising a sequence that is at least 55% identical to the sequence SEQ ID NO: 1, to the sequence SEQ ID NO: 2, to the sequence SEQ ID NO: 3 and/or to the sequence SEQ ID NO: 4, or a fragment thereof, having cysteine endoprotease activity, in order to decrease the cloudiness of a cereal-based beverage, fermented or not.

The present invention also has the object of using a malt extract comprising an endoproteasic activity to reduce the cloudiness of a cereal-based beverage, fermented or not.

Another object of the invention relates to the use of (i) at least one cysteine endoprotease as defined above, or (ii) a malt extract as defined above, in the preparation of a cereal-based beverage, fermented or not.

The present invention also relates to a method for preventing or reducing the cloudiness of a cereal-based beverage, fermented or not, comprising a step of adding (i) at least one cysteine endoprotease as defined above, or (ii) a malt extract as defined above, during the method for producing the beverage.

The present invention also relates to the use of (i) at least one cysteine endoprotease as defined above, or (ii) a malt extract as defined above, in order to increase the fermentation yield during the production of fermented cereal-based beverages.

The present invention also relates to a process for the manufacture of a cereal-based beverage, fermented or not, comprising a step of adding, in the wort or juice, (i) at least one cysteine endoprotease such as defined above, or (ii) a malt extract as defined above.

Another object of the invention relates to a cereal-based beverage obtainable by one of the methods according to the invention.

DETAILED DESCRIPTION OF THE INVENTION

Cereal-Based Beverage

By "beverage" is meant here beverages at all the stages of their preparation. Therefore, a beverage is not only a ready-to-consume beverage but also any composition used to prepare the beverage. Preferably, a beverage in the context of the invention is a beverage ready to be consumed.

By "cereal-based beverage" is meant here any beverage of which at least one of the raw materials used for its preparation comes from a cereal. The cereal-based beverage obtained in the context of the invention may thus be a barley, wheat, in particular wheat, oats, rye, corn, rice, sorghum, millet, pseudo-cereals such as quinoa or buckwheat, or mixtures thereof. Preferably, the cereal-based beverage obtained in the context of the invention is a barley or wheat-based beverage.

The cereal-based beverage obtained in the context of the invention may be a fermented or an unfermented beverage. Preferably, it is a fermented beverage.

The cloudiness observed during the storage of cereal-based beverages, fermented or not, is generally due to polyphenol-protein and/or protein-protein interactions. Accordingly, in a particular embodiment, the cereal-based or fermented beverage obtained within the scope of the invention comprises proteins and polyphenols.

The inventors have shown that cysteine endoproteases and/or malt extract are particularly effective in preventing or reducing beer cloudiness.

Accordingly, in a particular embodiment, the fermented or non-fermented cereal-based beverage is a liquid used in the production of the beer. In a particularly preferred manner, the cereal-based beverage, fermented or not, is a beer.

By "beer" is meant here the beers obtained from maize prepared from non-malted cereals, from maize prepared from malted cereals, or from maize prepared from a mixture of malted and not malted cereals. The term "beer" here covers low-fermentation beers, i.e. those whose fermentation is carried out at a temperature generally between 8 and 12° C., high fermentation beers, i.e. whose fermentation is generally carried out at a temperature between 20 and 25° C., beers of single, double or triple fermentation (whose fermentation temperatures are modified during fermentation), beers with spontaneous fermentation, i.e. whose fermentation does not require the addition of yeast to the wort, beers with mixed fermentation, i.e. fermentation which combines fermentation with a yeast and a bacterium (of the lactic or acidifying type) or with two yeasts, beers prepared with additives and beers with a range of alcohol levels of 0 to 10%.

Decreased Cloudiness

The terms "cloudiness" and "turbidity" are used interchangeably herein. The cloudiness may be measured by any technique well known to persons skilled in the art, typically by means of a turbidimeter, for example included in a tannometer. Briefly, in a turbidimeter, the radiated light is reflected by the existing particles (turbidity). The scattered light is then measured by a photodetector arranged at right angles (90°) with respect to the light source. The turbidity is expressed in NTU (Nephelometric Turbidity Units) or EBC (European Brewery Convention units), 1 NTU equivalent to 0.25 EBC. It is preferably evaluated at a temperature of −8° C. Turbidity is preferably measured using the Chapon test described in Chapon et al. (1993) J. Inst. Brew. 99: 49-56, in particular the "Alcohol-Chill-Test" test described in Chapon et al. (1993) J. Inst. Brew. 99: 49-56. Typically, 9.4 ml of sample are mixed with 0.6 ml of ethanol. After incubation preferably for at least 30 min, for example for 30 min or 40 min, at −8° C., the turbidity is measured at −8° C. on a turbidimeter, typically on a tannometer, as sold by the company Pfeuffer. The results are then typically expressed in EBC units.

The terms "decreased cloudiness", "turbidity reduction" and "clarification" are used interchangeably hereinafter. Preferably, cysteines endoproteases and the malt extract used in the context of the invention make it possible to reduce the cloudiness of the beverage to a significant degree when compared with the same untreated beverage.

Preferably, cysteines endoproteases and malt extract used in the context of the invention make it possible to reduce the turbidity of the beverage by at least 70% with respect to the same untreated beverage, more preferably at least 73%, at least 73%, at least 74%, at least 75%, at least 77%, at least 80%, at least 85%, at least 86%, or more preferably at least 93%, at least 94% or at least 95%, in particular when the turbidity is measured at −8° C., more particularly by means of the Chapon test as described above.

Preferably the cysteines endoproteases and the malt extract used in the context of the invention make it possible to reduce the cloudiness of the beverage compared to the same untreated beverage by at least 65 EBC units, at least 67 EBC units, at least 68 EBC units, at least 70 EBC units, at least 74 EBC units, at least 75 EBC units, at least 80 EBC units, at least 81 EBC units, at least 87 EBC units, at least 89 EBC units, at least 90 EBC units, at least 94 EBC units, at least 95 EBC units, at least 100 EBC units, at least 102 EBC units, or at least 103 EBC units, especially when the turbidity is measured at −8° C., more particularly by means of the Chapon test as described above.

Increased Fermentation Yield

By "increased fermentation yield", is meant here that for equivalent fermentation time, there are fewer fermentable sugars still present in the wort compared to different controls, in particular positive and/or negative controls. Negative controls, preferably two negative controls, may consist of a wort without any addition and a wort with the addition of crude extract of heat-denatured barley malt, while the positive control may be constituted by a wort with the addition of Brewers Clarex®.

The monitoring of the fermentation is typically carried out by monitoring the yeast population and the percentage by mass of the dry extract of the wort, expressed in Plato degrees (noted °Plato). 1°Plato corresponds to 1 g of dried soluble solids (mainly fermentable sugars) per 100 g of wort. The amount of sugar initially included in the wort determines the amount of alcohol and carbon dioxide in the beer produced. The Plato degree is typically measured by means of an automatic densimeter (Anton-Paar DMA35 densimeter).

The inventors have thus shown that the cysteines endoproteases and the malt extract used in the context of the invention make it possible to achieve a °Plato of at most 1 on D0+8 when it is added during the fermentation step.

Thus, preferably, cysteines endoproteases or the malt extract according to the invention increase the fermentation yield in order to reach a °Plato 8 days after the start of the fermentation, of at most 1, more preferably at most 0.8, at most 0.7, at most 0.6, at most 0.5 or at most 0.2°Plato, in particular when the fermentation is carried out at a temperature of approximately 13° C., and, in particular, when a wort at 11°Plato is produced by "EBC congress" type brewing.

Cysteine Endoprotease

By "cysteine endoprotease" or "cysteine endopeptidase" is meant here an enzyme of class EC 3.4.22, the nucleophilic amino acid residue of the catalytic triad, which is a cysteine and cleaves the proteins within the peptide chain.

The cysteine endoprotease(s) used in the invention comprises, or consists of, at least 55% identical, more preferably at least 60% identical, at least 65% identical, at least 70% identical, at least 75% identical, at least 80% identical, at least 85% identical, at least 90% identical, at least 90% identical, 91, 92, 93, 94, 95, 96, 97, 98, 99 or 100% identical to the sequence SEQ ID NO: 1, to the sequence SEQ ID NO: 2, to the sequence SEQ ID NO: 3 and/or to the sequence SEQ ID NO: 4, or a fragment thereof exhibiting a cysteine endoprotease activity.

By "sequence at least x % identical to a reference sequence", is meant here that the sequence is identical to the reference sequence or differs from the reference sequence by up to 100-x amino acid alterations for each 100 amino acids of the reference sequence. The alterations of amino acids with respect to the reference sequence may be substitutions, deletions and/or insertions of one or more amino acids, and at positions so that these modifications do not significantly affect the enzymatic activity of the enzymes. The substitutions may, in particular, correspond to conservative substitutions or to substitutions of natural amino acids by unnatural amino acids or pseudo-amino acids. In a particular embodiment, the protein sequence differs from the reference sequence only by the presence of conservative substitutions. Conservative substitutions are substitutions of amino acids of the same class, such as amino acid substitutions to uncharged side chains (such as asparagine, glutamine, serine, cysteine, and tyrosine) amino acids to basic side chains (such as lysine, arginine, and histidine), from amino acids to acidic side chains (such as aspartic acid and glutamic acid), from amino acids to side chains (such as alanine, valine, leucine, isoleucine, proline, phenylalanine, methionine and tryptophan).

The alignment and determination of the percentage identity may be done manually or automatically using, for example, the Needle program which is based on the Needleman and Wunsch algorithm, described in Needleman and Wunsch (1970) J. Mol. Biol. 48: 443-453, with, for example, the following parameters for the comparison of protein sequences: comparison matrix: BLOSUM62, gap open penalty=10, gap extend penalty=0.5, end gap penalty=false, end gap open penalty=10; end gap extend penalty=0.5, and the following parameters for comparison of nucleic sequences: comparison matrix: DNAFULL; gap open penalty=10, gap extend penalty=0.5, end gap penalty: false, end gap open penalty=10, end gap extend penalty=0.5.

The sequences SEQ ID NO: 1 and SEQ ID NO: 2 correspond to the amino acid sequences of cysteine endoproteases EP-A of barley.

EP-A barley cysteine endoprotease is described in Koehler and Ho (1988) Plant Physiol. 87: 95-103. EP-A has an apparent molecular weight of 37 kDa and exhibits optimum activity at pH 5.0 and a temperature of 45° C. It is induced by gibberellic acid. Its cleavage site on recombinant C-type hordeins was characterized in Davy et al. (1998) Plant Physiol. 117: 255-261: EP-A cuts the hordeins after the amino acids arginine and glutamine, with a preference for arginine. The presence at the cleavage site of an amino acid such as phenylalanine, leucine or valine before arginine or glutamine promotes hydrolysis, while the presence of proline before or after these two residues, decreases its catalytic efficiency but does not inhibit it. The catalytic specificities of EP-A on prolamines remain poorly characterized, although likely on the basis of the sequence identity of EP-A and EP-B (52% for preproproteins and 60% for the matured protein) and strict conservation of the active site amino acids involved in the catalysis and in the anchoring of the peptide segment according to the crystallographic structure of the EP-B-leupeptin complex described by Bethune et al. (2006), wherein EP-A and EP-B have identical catalytic specificities. Two variants of cysteine endoprotease EP-A of barley were identified: these are variants of sequences:

```
                                                    (SEQ ID NO: 1)
MWRCILLSAVVVALALAPAPALGVPFTEKDLASEESLRGLYERWRSHYTV

SRRGLGADAEERRFNVFKENARYVHEGNKRDRPFRLALNKFADMTTDEFR

RTYAGSRVRHHLSLSGGRRGDGGFRYADADNLPPAVDWRQKGAVTAIKDQ

GQCGSCWAFSTIVAVEGINKIRTGKLVSLSEQELMDCDNVNNQGCEGGLM

DYAFQFIQKNGITTESNYPYQGEQGSCDQAKENAQAVTIDGYEDVPANDE

SALQKAVAGQPVSVAIDASGQDFQFYSEGVFTGECSTDLDHGVAAVGYGA

TRDGTKYWIVKNSWGEDWGEKGYIRMQRGVSQTEGLCGIAMQASYPTKSA

PHASTVREGSHTDEL
and
                                                    (SEQ ID NO: 2)
MWRCILLSAVVVALALAPAPALGVPFTEKDLASEESLRGLYERWRSHYTV

SRRGLGADAEERRFNVFKQNARYVHEGNKRDMPFRLALNKFADMTTDEFR

RTYAGSRVRHHLSLSGGRRGDGGFRYGDADNLPPAVDWRQKGAVTAIKDQ

GQCGSCWAFSTIVAVEGINKIRTGKLVSLSEQELMDCDNVNNQGCDGGLM

DYAFQFIQKNGITTESNYPYQGEQGSCDQAKENAQAVTIDGYEDVPANDE

SALQKAVAGQPVSVAIDASGQDFQFYSEGVFTGECSTDLDHGVAAVGYGA

TRDGTKYWIVKNSWGEDWGEKGYIRMQRGVSQTEGLCGIAMQASYPTKSA

PHASTVREESHTDEL.
```

Different domains have been identified in the protein sequences of EP-A. Thus, amino acids 1 to 23 of SEQ ID NO: 1 or SEQ ID NO: 2 correspond to the signal peptide and amino acids 128 to 365 of SEQ ID NO: 1, or SEQ ID NO: 2 corresponds to the mature chain SEQ ID NO: 5 and 6). The catalytic site of EP-A was not characterized. The catalytic site may, however, be deduced by homology with EP-B as containing the following amino acids: cysteine 29, histidine 164, serine 28, glycine 71, aspartate 163, asparagine 185, glutamine 23 numbered on the basis of the mature protein sequence of sequence SEQ ID NO: 5 or SEQ ID NO: 6.

The sequences SEQ ID NO: 3 and SEQ ID NO: 4 correspond to the amino acid sequences of cysteine endoproteases EP-B of barley.

Cysteine endoprotease EP-B barley is described in Koehler and Ho (1990) Plant Physiol. 94: 251-258. EP-B has an apparent molecular weight of 30 kDa (Davy et al., (1998) Plant Physiol. 117: 255-261) and exhibits optimum activity at pH 4.5 and a temperature of 40° for model protein substrates (azocasein or hemoglobin). Under these optimal conditions, the hordeins are typically cleaved into multiple fragments with a molecular mass of between 2000 and 25,000 Daltons. EP-B is induced by gibberellic acid. Its cleavage site on recombinant C-type hordeins was characterized in Davy et al. (1998) Plant Physiol. 117: 255-261: EP-B cuts the hordeins after the amino acids arginine and glutamine, with a preference for arginine for primary cuts. The presence, at the cleavage site, of an amino acid such as phenylalanine, leucine or valine before arginine or glutamine, promotes hydrolysis. In contrast to EP-A, EP-B retains good catalytic activity despite the presence of proline after these two arginine or glutamine residues. Secondary cleavage sites may be demonstrated when the hydrolysis of C-hordein by EP-B is prolonged. The endoprotease may cleave after glutamine, arginine, tyrosine, glycine, glutamic acid, serine, histidine, leucine. It does not apparently cut N- or C-terminal of a proline in the case of C-hordein (Davy et al., 1998) and therefore may not be assimilated to endoprolidase. Similar results have been obtained for the hydrolysis of α2-gliadin by recombinant EP-B and shows a clear preference for glutamine C-terminal cuts (Bethune et al., 2006). The specificity of cleavage of cysteine endoproteases from cereals is also very different from that of other cysteine endoproteases such as papain which is used to decrease the cloudiness of beer. Papain is, in fact, relatively non-specific (Kimmel and Smith (1954) J. Biol. Chem. 207: 515-531).

Two variants of cysteine endoprotease EP-B of barley have been identified: these are variants of sequences:

(SEQ ID NO: 3)
MGLLSKKLLVASMVAAVLAVAAVELCSAIPMEDKDLESEEALWDLYERWQ

SAHRVRRHHAEKHRRFGTFKSNAHFIHSHNKRGDHPYRLHLNRFGDMDQA

EFRATFVGDLRRDTPAKPPSVPGFMYAALNVSDLPPSVDWRQKGAVTGVK

DQGKCGSCWAFSTVVSVEGINAIRTGSLVSLSEQELIDCDTADNDGCQGG

LMDNAFEYIKNNGGLITEAAYPYRAARGTCNVARAAQNSPVVVHIDGHQD

VPANSEEDLARAVANQPVSVAVEASGKAFMFYSEGVFTGDCGTELDHGVA

VVGYGVAEDGKAYVVTVKNSWGPSWGEQGYIRVEKDSGASGGLCGIAMEA

SYPVKTYNKPMPRRALGAWESQ
and (SEQ ID NO: 4)
MGLLSKKLLVASMVAAVLAVAAVELCSAIPMEDKDLESEEALWDLYERWQ

SAHRVRRHHAEKHRRFGTFKSNAHFIHSHNKRGDHPYRLHLNRFGDMDQA

EFRATFVGDLRRDTPSKPPSVPGFMYAALNVSDLPPSVDWRQKGAVTGVK

DQGKCGSCWAFSTVVSVEGINAIRTGSLVSLSEQELIDCDTADNDGCQGG

LMDNAFEYIKNNGGLITEAAYPYRAARGTCNVARAAQNSPVVVHIDGHQD

VPANSEEDLARAVANQPVSVAVEASGKAFMFYSEGVFTGECGTELDHGVA

VVGYGVAEDGKAYWTVKNSWGPSWGEQGYIRVEKDSGASGGLCGIAMEAS

YPVKTYSKPKPTPRRALGARESL.

Different domains have been identified in EP-B protein sequences. Thus, amino acids 1 to 28 of SEQ ID NO: 3 or SEQ ID NO: 4 correspond to the signal peptide, amino acids 29 to 130 of SEQ ID NO: 3 or SEQ ID NO: 4 correspond to the activation propeptide and amino acids 131 to 371 of SEQ ID NO: 3 (sequence SEQ ID NO: 7) or 131 to 373 of SEQ ID NO: 4 (sequence SEQ ID NO: 8) correspond to the mature chain. The EP-B catalytic site was further characterized. It mainly involves cysteine 158 (cysteine 28 for the mature protein of sequence SEQ ID NO: 7 or 8) and histidine 297 (histidine 167 for the mature protein of sequence SEQ ID NO: 7 or cys 8) of SEQ ID NO: 3 or SEQ ID NO: 4.

In these two proteins, aspartate 296 (aspartate 166 in the mature protein) is involved in the positioning of the substrate with respect to cysteine 158 (cysteine 28 in the mature protein) catalyst (Bethune et al., 2006).

The cysteine endoprotease used in the context of the invention may have cysteine endoprotease A or cysteine endoprotease B activity.

In a particularly preferred manner, the cysteine endoprotease(s) used in the invention is (i) a cysteine endoprotease A comprising, or consisting of a sequence that is identical at least 55%, or at least 60, 65, 70, 75, 80, 85, 90, 91, 92, 93, 94, 95, 96, 97, 98, 99 or 100% to the sequence SEQ ID NO: 1 and/or SEQ ID NO: 2, and/or a fragment thereof having cysteine endoprotease A activity, and/or (ii) a cysteine endoprotease B comprising, or consisting of a sequence that is identical, at least 55%, or at least 60, 65, 70, 75, 80, 85, 90, 91, 92, 93, 94, 95, 96, 97, 98, 99 or 100% to the sequence SEQ ID NO: 3 and/or to SEQ ID NO: 4, and/or a fragment thereof having cysteine endoprotease B activity.

Most preferably of all, the cysteine endoprotease(s) used in the invention is (i) cysteine endoprotease EP-A of barley comprising, or consisting of, the sequence SEQ ID NO: 1 or SEQ ID NO: 2, and/or (ii) cysteine endoprotease EP-B of barley comprising, or consisting of, the sequence SEQ ID NO: 3 or SEQ ID NO: 4.

By "fragment" of a reference sequence is meant here a sequence which has a size less than the reference sequence. In the context of the present invention, the fragments may for example have a size between 230 and 373 amino acids, 235-371 amino acids, 236-365 amino acids, 237-350 amino acids, 239-300 amino acids, from 240 to 290 amino acids, from 250 to 280 amino acids or from 260 to 270 amino acids. Preferably, within the scope of the invention, the fragments contain the active site of the enzyme from which they are derived. The fragments used in the context of the invention may be obtained by enzymatic or non-enzymatic cleavage of the mature enzyme or of the proprotein from which they are derived, while preserving or enhancing the specificity and the endoprotease efficiency.

The fragments used in the context of the present invention exhibit endoprotease cysteine activity. Fragments of the above-defined protein sequences exhibiting endoprotease cysteine activity may be identified by persons skilled in the art through routine techniques. In fact, as is well known to persons skilled in the art, cysteine endoprotease comprise a peptide signal, and the endoprotease cysteine activity is thus located at the level of the mature cysteine endoprotease chain.

Thus, in a particularly preferred embodiment, the cysteine endoprotease fragment used within the scope of the invention comprises, or consists of a sequence that is identical, at least 55%, or at least 60, 65, 70, 75, 80, 85, 90, 91, 92, 93, 94, 95, 96, 97, 98, 99 or 100% to the sequence SEQ ID NO: 5, SEQ ID NO: 6, SEQ ID NO: 7 and/or SEQ ID NO: 8, wherein the fragment exhibits endoprotease cysteine activity.

Moreover, since it is well known to persons skilled in the art, the catalytic site of the endoprotease cysteine is located within a pocket containing cysteine and a histidine involved in catalysis, and various amino acids involved in the binding and/or recognition of the cleavage site as described above for EP-A. Fragments of the above-defined protein sequences having endoprotease cysteine activity will therefore preferably comprise, or preferably consist of, amino acid residues of the cysteine endoprotease catalytic site defined above.

Thus, in a preferred embodiment, the cysteine endoprotease fragment used within the scope of the invention comprises, or consists of, a fragment of the preprotein or mature protein or any functional protein fragment containing the amino acid residues of the catalytic site described above.

Persons skilled in the art may then verify that these fragments exhibit endoprotease cysteine activity by measuring their activity through techniques well known in the prior art, for example using cysteine endoprotease specific inhibitors such as E64 (trans-epoxysuccinyl-L-leucocylamido-(-4-guanidino) butane).

The techniques for measuring endoproteasic cysteine activity are indeed well known to persons skilled in the art. Typically, they comprise colorimetric or fluorimetric techniques using di- or tripeptides with a chromophore or fluorophore, techniques using cereal protein proteins (prolamins) or fragments of these proteins coupled to an analysis of the peptides produced by spectrometry mass. Typically, endoprotease cysteine activity may be measured using a fluorescent peptide such as N-CBZ (benzyloxycarbonyl)-Phe (phenylalanine)-Arg (arginine)-AMC (7-amido-4-methylcoumarin) in a 50 mM citrate buffer (pH 4 containing 2 mM cysteine and 2 mM β-mercaptoethanol). The substrate, N-CBZ-Phe-Arg-AMC, is solubilized in DMSO at a concentration of 100 µM, while 10 µl are added to a quartz cuvette containing 2 mL of the citrate buffer. Between 10 and 30 µl of enzymatic solution are typically added and the fluorescence increase is measured over time (excitation 360 nm, emission 460 nm) at a temperature of 20° C. The initial rate of reaction is deduced from the slope measurement of the fluorescence intensity curve as a function of time. The total fluorescence was measured using a 0.2 µM papain solution.

The at least one endoprotease cysteine used in the context of the invention may be used in isolated or purified form.

By "isolated" or "purified" is meant here a cysteine endoprotease taken from its natural environment. For example, a cysteine endoprotease recombinantly produced in host cells is considered isolated in the context of the invention, as is a recombinant or native polypeptide which has been purified substantially by any suitable technique.

The at least one cysteine endoprotease used in the context of the invention may be in isolated form. It may, however, be mixed in carriers or diluents which will not interfere with the desired effect of this enzyme and will therefore always be considered as isolated.

The at least one cysteine endoprotease used within the scope of the invention may also be in a more substantially purified form which will include the at least one cysteine endoprotease in a preparation in which more than 70%, or more than 80%, 90% 95%, 98% or 99% of the proteins in the preparation is the at least one cysteine endoprotease.

The cysteine endoprotease used in the context of the invention may be in the form of a crude or purified natural product, a product obtained by chemical synthesis, a product obtained by a recombinant technique from a eukaryotic or prokaryotic host, such as a bacterial, yeast, fungal, plant, insect or mammalian cell.

In a recombinant production method, a vector containing a nucleic acid encoding a cysteine endoprotease is preferably transferred into a host cell which is cultured under conditions allowing expression of the corresponding protein. The enzyme produced may then be recovered and purified. The nucleic acid sequence of interest may be inserted into an expression vector, in which it is operatively linked to one or more elements enabling its expression, or regulation of its expression, such as in particular promoters, activators and/or transcription terminators. The signals controlling the expression of the nucleotide sequences (promoters, activators, termination sequences . . . ) are chosen as a function of the cellular host used. For this purpose, the nucleotide sequences encoding the protein of interest may be inserted into vectors with autonomous replication within the chosen host, or integrative vectors of the chosen host. Such vectors will be prepared according to methods commonly used by persons skilled in the art and the resulting clones may be introduced into a suitable host by standard methods such as electroporation or calcium phosphate precipitation. Examples of host cells include, but are not limited to, human cells such as HEK293, PER.C6, non-human mammalian cells such as CHO, COS, MDCK, insect cells such as SF9, bacteria such as *E. coli*, fungus and/or yeast strains such as L40 and Y90.

In a particular embodiment, the at least one cysteine endoprotease used in the context of the invention may be obtained from plant extracts in which it is naturally produced.

The at least one cysteine endoprotease used in the context of the invention may thus be obtained from protoplasts of aleuronic cells or from a cell culture of the aleurone layer. Techniques for culturing protoplasts of aleuronic cells or the aleurone layer are well known to persons skilled in the art and described, for example, in Chrispeels & Varner (1967) Plant Physiol. 42: 398-406 and Taiz & Jones (1971) Planta 101: 95-100. Since cysteine endoproteases are induced by gibberellic acid, the cells of the aleurone layer are grown in a particular embodiment in the presence of gibberellic acid, preferably at a concentration of about 1 µM.

The germination of cereal grains inducing expression of cysteine endoproteases, the at least one cysteine endoprotease used in the context of the invention, may also be obtained from germinated cereal grains, in particular from cereal malt, such as described in the "Malt extract" section below.

A cysteine endoprotease used in the context of the invention may be obtained from recombinant cell cultures, from plant cell cultures or from plants or parts of plants, in particular from lysates and cell extracts, plants or parts of plants, or the supernatant of the culture medium, by techniques well known to persons skilled in the art, and used individually or in combination, such as precipitation with ammonium sulphate or with ethanol, acid extraction, chromatographic methods, immunoaffinity techniques using specific mono- or polyclonal antibodies, and the like.

It may also be obtained in crude form by simple extraction from cultures of recombinant cells, from plant cell cultures or from plants or parts of plants, or from the supernatant of the culture medium.

Thus, in a particular embodiment, the at least one cysteine endoprotease is used in the form of malt extract as defined in the "malt extract" section below.

Malt Extract

By "malt" is meant here a germinated cereal obtained through a malting process.

The malt may be obtained by any malting technique well known to persons skilled in the art. Malting takes place typically in 4 steps, including soaking, which moistens the grain, the germination during which the grain begins to germinate and gives rise to "green malt", the oasting where the green malt is dried to obtain a dry malt, and the degermage where the malt is rid of its rootlets.

Preferably, the malt used in the context of the invention is a dry malt. In a particularly preferred manner, the malt used in the context of the invention is a dry malt obtained after 5 to 11 days of germination.

The malt used in the context of the invention is preferably a cereal malt, in particular a malt of barley, rye or wheat, more preferably a malt of barley, more particularly a barley winter malt or a spring barley malt.

The malt used in the context of the invention may be a diastatic or non-diastatic malt.

By "malt extract" is meant here a preparation obtained by extraction of a malt with a suitable solvent such as, for example, water, aqueous buffers, ethanol, a mixture of those oils or other suitable aqueous buffers well known in the field of plant extractions. The malt extract used in the context of the invention may, in particular, be an extract of malt, preferably dry malt, optionally concentrated.

The malt extract used in the context of the invention may be in freeze-dried form and optionally resuspended before use.

The malt extract used in the context of the invention comprises endoprotease activity.

By "endoprotease activity" is meant here a protease enzymatic activity capable of cleaving a protein or a peptide within the peptide chain. Techniques for demonstrating endoprotease activity are well known to persons skilled in the art and described in the above cysteine endoprotease section.

Preferably, the malt extract comprising an endoprotease activity used in the context of the invention results in a decrease in the turbidity of a fermented or non-fermented cereal-based beverage, as defined in the section entitled "Cereal-based beverage" above, compared with an untreated beverage, of at least 70%, more preferably at least 75%, at least 80%, at least 85%, at least 90%, or still more preferably at least 95%, especially when the turbidity is measured at −8° C., more particularly by means of the Chapon test as described in the "Decreased cloudiness" section above.

Preferably, the malt extract comprising an endoprotease activity and used in the context of the invention results in a decrease in the turbidity of a fermented or non-fermented cereal-based beverage, as defined in the section entitled "Cereal-based Beverage", compared with an untreated beverage of at least 65 EBC units, more preferably at least 70 EBC units, at least 75 EBC units, at least 80 EBC units, at least 85 EBC units, at least 90 EBC units, at least 95 EBC units, or at least 100 EBC units, especially when turbidity is measured at −8° C., more particularly using the Chapon test as described in the section "Decreased cloudiness" above.

A malt extract having such characteristics may typically be a crude malt extract obtained by recovering the centrifugation supernatant of a malt, as defined above, ground and suspended in an aqueous solution.

More preferably, a malt extract having such characteristics is a processed malt extract obtained by recovery and centrifugation filtration of a crude malt extract as defined above, treated by differential precipitation with ammonium sulphate, in particular treated with ammonium sulphate saturation of between 15% and 20%, preferably 26%, and optionally at least 50%, preferably 89%, saturation with ammonium sulphate, or saturated by any percentage with ammonium sulphate as is well known to persons skilled in the art.

As shown in the examples, the inventors have indeed demonstrated that an extract of malt obtained by one of these techniques makes it possible to reduce the cloudiness of a cereal-based beverage, fermented or not, in a proportion conforming to the one mentioned above. The malt extract used in the context of the invention may, however, be obtained by any technique comprising additional extraction and/or purification steps that are well known to persons skilled in the art, such as techniques for ion exchange chromatography, size exclusion chromatography or hydrophobic interaction chromatography.

The inventors have also shown that an extract of malt obtained by one of these techniques comprises an endoprotease cysteine activity.

Preferably, the malt extract used in the context of the invention therefore comprises an endoprotease cysteine activity, as defined in the cysteine endoprotease section above. More preferably, the malt extract used within the scope of the invention comprises cysteine endoprotease A and/or cysteine endoprotease B activity as defined in the above cysteine endoprotease section.

The inventors have also shown that an extract of malt obtained by one of these techniques makes it possible to increase the fermentation yield during the manufacture of fermented cereal-based beverages.

Method for Preventing or Reducing Cloudiness and Method for Producing a Beverage The present invention also relates to a method for preventing or reducing the cloudiness of a cereal-based beverage, fermented or not, as defined in the above section "Cereal-based beverage", wherein it comprises the addition of (i) at least one cysteine endoprotease as defined in the above section "Cysteine endoprotease", or (ii) a malt extract as defined in the above section "Malt extract" during the beverage manufacturing process.

The present invention also relates to the use of (i) at least one cysteine endoprotease as defined in the section "Cysteine endoprotease" above, or (ii) a malt extract as defined in the section "Malt extract" above in the production of a cereal-based, fermented or unfermented beverage, as defined in the above section "Cereal-based beverage".

The present invention also relates to a method for producing a cereal-based beverage, fermented or not, as defined in the above section "Cereal-based beverage", comprising a step of adding (i) at least one cysteine endoprotease as defined in the section above "Cysteine endoprotease" or (ii) a malt extract as defined in the above section "Malt extract", especially in juice or wort.

The steps of a method for producing a fermented or non-fermented cereal-based beverage are well known to persons skilled in the art and may vary according to the beverage manufactured, in particular according to whether the beverage is a fermented beverage or not.

The prevention or reduction of the cloudiness of the beverage obtained by virtue of the present invention being obtained due to an enzymatic activity, the step of adding (i) at least one cysteine endoprotease as defined in the section "Cysteine endoprotease" above or (ii) a malt extract as defined in the above section "Malt extract", may be carried out at any stage of the method for producing the beverage, wherein it is not followed by a step capable of destroying the endoproteasic activity.

Such steps capable of destroying the endoprotease activity are well known to persons skilled in the art and include, for example, treatment steps at elevated temperatures, in particular at temperatures above 62° C., in particular above 65° C., or even 68° C., such as saccharification or boiling steps.

Thus, in a particular embodiment, the additional step is carried out after the saccharification and/or boiling step of the method for producing the beverage.

In a particular embodiment, when the manufactured beverage is a fermented cereal beverage, especially when the beverage made is a beer, the at least one cysteine endoprotease or the malt extract is added during the fermentation step of the method for producing the beverage, preferably at the beginning of the fermentation step of the beverage manufacturing process.

As is well known to persons skilled in the art, several types of fermentation may be used to produce a fermented cereal-based beverage, particularly a beer. Thus, the at least one cysteine endoprotease or malt extract may be added during a low fermentation step, during a high fermentation step, or during a spontaneous fermentation step.

Preferably the beverage being produced is thus brought into contact with the at least one cysteine endoprotease or the malt extract for a time suitable to allowing the enzymes to degrade the proteins responsible for the cloudiness. Such a duration will depend on the incubation conditions of the cysteine endoprotease or malt extract with the beverage being processed, particularly the temperature and pH conditions.

The inventors have shown that the usual duration of the fermentation step during the process of making a beer, whether low or high fermentation, is particularly suitable for obtaining the prevention or reduction of the cloudiness of the beer as defined in the section "Decreased cloudiness" above.

Thus, in a particular embodiment, the beverage being manufactured is brought into contact with the at least one cysteine endoprotease or the malt extract for 8 to 12 days, preferably for 10 days, at a temperature of between 10 and 12° C., preferably at a temperature of 12° C., preferably at a starting pH of 5.3-5.4, wherein the final pH may reach 4.2-4.3 due to the natural evolution of pH during fermentation.

In another particular embodiment, the beverage being manufactured is brought into contact with the at least one cysteine endoprotease or the malt extract for 4 to 8 days, preferably for 6 days, at a temperature of between 20 and 25° C., preferably at a starting pH of 5.3-5.4.

Typically, the method for producing beer according to the invention comprises the following steps:

(a) a malting or supply of malt step,
b) a step of crushing or milling the malt obtained in step a),
c) a step of mixing the milled malt in step b) with preferably tempered water to form a mash,
d) a step of saccharifying the mash obtained in step c) to form a wort, preferably by decoction, infusion by increments or simple infusion,
e) a filtration step for obtaining the primary wort,
f) a boiling step comprising a bittering and flavoring hopping step,
g) a "whirlpool" tangential separation or centrifugation step to separate the cloudiness from the wort,
h) a step of cooling, seeding and oxygenating the wort,
i) a fermentation step, in particular a low, high or spontaneous fermentation step, in the presence of yeasts, during which step, preferably at the beginning, the at least one cysteine endoprotease or the malt extract is added,
j) a step of storing the fermented product obtained in step g),
k) a step of filtration and separation of the yeasts, and
l) a conditioning step.

Steps a) to h) and j) to l) may be carried out conventionally under conditions well known to persons skilled in the art.

In the fermentation step i), the wort is preferably brought into contact with the at least one cysteine endoprotease or the malt extract for 8 to 12 days, preferably for 10 days, at a temperature of between 8 and 14° C., preferably at a temperature of 12° C., preferably at a starting pH of 5.3-5.4, or for 4 to 8 days, preferably for 6 days, at a temperature between 15 and 20° C., preferably at a starting pH of 5.3-5.4.

The methods according to the invention may further comprise a step of adding an auxiliary enzyme which makes it possible to reduce or prevent the formation of a cloudiness. Such auxiliary enzymes to reduce or prevent the formation of cloudiness are well known to persons skilled in the art, and include, for example, Brewers Clarex® marketed by DSM, or papain.

The beverages obtained by the methods according to the invention differ from the beverages obtained by the manufacturing processes of the prior art insofar as they contain cysteine endoprotease or malt extract introduced during the methods according to the invention, whether the enzymes are inactivated or not, and the cysteine endoprotease or malt extract modifies the peptide and protein composition of the product obtained, resulting in the prevention or reduction of the formation of the cloudiness, usually due to the presence of residual proteins.

The subject of the present invention is thus also to produce a cereal-based beverage, in particular fermented or not, as defined in the above section "Cereal based beverages", preferably a beer, obtainable by the methods according to the invention.

The present invention will be illustrated in more detail by the figures and examples below.

DESCRIPTION OF SEQUENCES

| SEQ ID NO: | Description |
| --- | --- |
| 1 | Protein sequence of a first variant of barley EP |
| 2 | Protein sequence of a second variant of barley EP |
| 3 | Protein sequence of a first variant of barley EP |
| 4 | Protein sequence of a second variant of barley EP |
| 5 | Mature chain of a first variant of barley EP |
| 6 | Mature chain of a second variant of barley EP |
| 7 | Mature chain of a first variant of the barley EP |
| 8 | Mature chain of a second variant of the barley EP |

EXAMPLES

Example 1: Decreased Beer Cloudiness with Different Types of Barley Malt

This example shows that an extract of malt obtained from different types of barley may be used to clarify the beer.

Material and Methods

Extraction 50 g of finished malt of various types of barley were extracted into 200 mL of 0.1 M citrate buffer, pH 4.3, stored in a refrigerator at 4° C. They were blended in a blender for 40 seconds at maximum speed and then centrifuged at 3660 rpm for 10 min at 14° C. The supernatant was recovered and filtered with a filter paper to remove the suspended particles.

Non-Stabilized Beer

The beer used in this example is Fink'bräu Beer 33 cL in a can kept at room temperature (21° C.), filtered on filter paper, and degassed for 20 minutes in an ultrasonic bath.

Samples

The positive control (T+) corresponds to 0.75 mL of Brewers Clarex® diluted 1/25+non-stabilized beer qsp 50 mL.

The negative control (T−) corresponds to 4 mL of 0.1 M citrate buffer pH 4.3+qsp 50 mL of non-stabilized beer.

The samples tested included the following extracts of the barley malts: Metaxa 3086 Ngt 1, Metaxa 3352 Ngt 1, Esterel 23036 B2P1, Esterel 23145 B1PO, Arturio 23005 B2PR, Arturio 23182 B1PO, Azurel 23054 B2PR, Azurel 23108 B2PR, Cervoise 23094 Ngt 1, Cervoise 3453 Ngt 1, Cartel 2965 Ngt 1, Cartel 3259 Ngt 1, Béatrix 23050 B2SA, Béatrix 23189 B2SA, Sébastian 993 Ngt 2, Sébastian 23119 B2P1, Grace 23076 B3ST, Grace 23219 B3ST, Prestige 23077 B3ST, Chill 23151 B3ST, Tipple 23192 B2PR, Tipple 23249 B2SA, Chamonix 404 Ngt 2, Chamonix 3227 Ngt 1, Charmey 436 Ngt 2, Charmey 897 Ngt 2, Henley 3319 Ngt 1, Henley 3328 Ngt 1.

The samples tested consist of 4 mL extract+non-stabilized beer qsp 50 mL.

The mixtures were incubated for 17 h in a water bath at 37° C.

Chapon Test

Controls and samples were incubated at 37° C. for a minimum of 5 h. In transparent plastic test tubes (polystyrene), 0.6 mL of 96% ethanol (=6%) was mixed with qsp 10 mL of sample (×2).

The mixture was incubated for 30 min at −8° C. in a cryostat bath.

Turbidity was measured at −8° C.

Results

Figure 9:
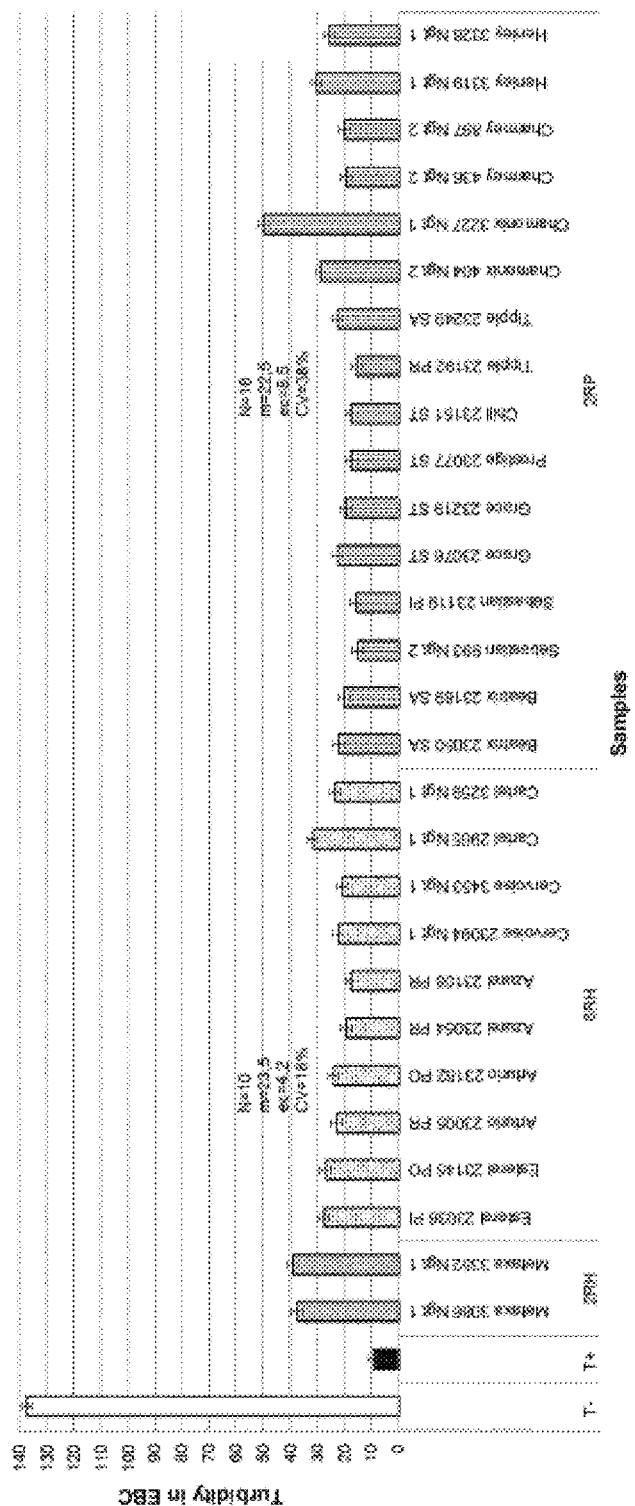
FIG. 9: Effect on the colloidal cloudiness of the beer (Chapon test) of the various extracts tested in Example 1.

The results are shown in FIG. 9. These results show that a decrease in turbidity is observed regardless of the type of barley from which the malt extract was obtained.

Example 2: Reduction of Beer Cloudiness with Wheat Malt

This example shows that a wheat malt extract may be used to clarify the beer.

Material and Methods

Extraction 50 g of finished malt of various types of barley were extracted into 200 mL of 0.1 M citrate buffer, pH 4.3, stored in a refrigerator at 4° C. They were blended in a blender for 40 seconds at maximum speed and then centrifuged at 3660 rpm for 10 min at 14° C. The supernatant was recovered and filtered with a filter paper to remove the suspended particles.

Non-Stabilized Beer

The beer used in this example is Fink'bräu Beer 33 cL in a can kept at room temperature (21° C.), filtered on filter paper, and degassed for 20 minutes in an ultrasonic bath.

Samples

The positive control (T+) corresponds to 0.75 mL of Brewers Clarex® diluted 1/25+non-stabilized beer qsp 50 mL.

The negative control (T−) corresponds to 4 mL of 0.1 M citrate buffer pH 4.3+qsp 50 mL of non-stabilized beer.

The samples tested include the following barley malt extracts: barley malt Chill 22304 B2BR, barley malt Arturio 23175 B1CA, barley malt diastasic Arturio 23112 B2BR, wheat malt Apache 23086 (Arcis sur Aube) and wheat malt Bagou (Arcis sur Aube).

The samples tested consist of 0.5, 1, 2, 3 or 4 mL extract+non-stabilized beer qsp 50 mL.

The mixtures were incubated for 17 h in a water bath at 37° C.

Chapon Test

The controls and samples were incubated at 37° C. for a minimum of 5 h. In transparent plastic test tubes (polystyrene), 0.6 mL of 96% ethanol (=6%) was mixed with qsp 10 mL of sample (×2).

The mixture was incubated for 30 min at −8° C. in a cryostat bath.

Turbidity was measured at −8° C.

Results

Figure 10:
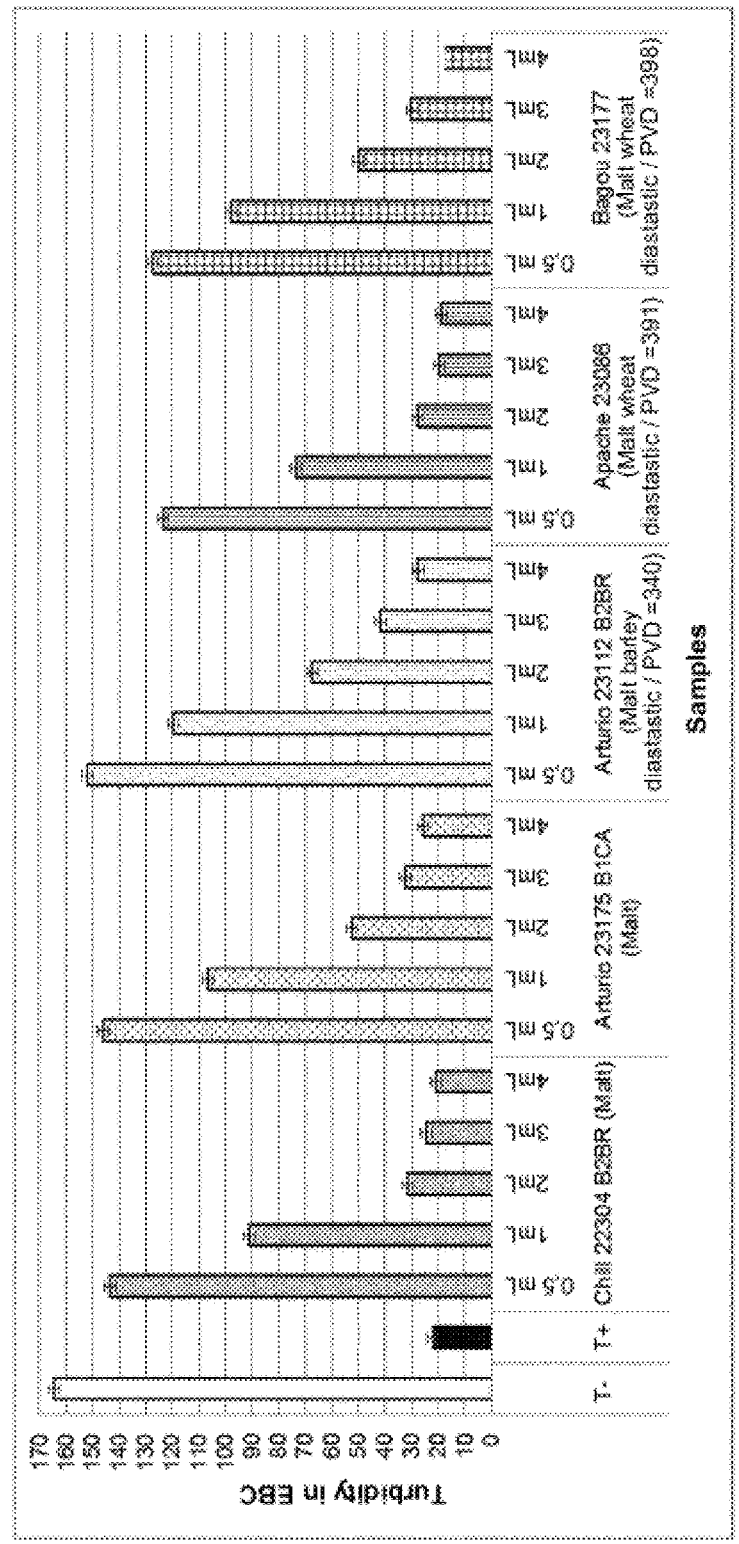
FIG. 10: Effect on the colloidal cloudiness of the beer (Chapon test) of the various extracts tested in Example 2.

The results are shown in FIG. 10. These results show that a decrease in turbidity is also observed with diastatic wheat malt, as well as diastatic barley malt.

Example 3: Identification in the Malt Extract of Enzymes Responsible for the Effect on Turbidity This example shows the effect of malt extracts on beer cloudiness and the involvement of cysteine barley endoproteases in this effect.

Materials and Methods

Materials

The malt used for the various experiments was obtained from barley grains of the variety Beatrix (*Hordeum vulgare*) malted by the Soufflet malt (Nogent sur Seine/Aube) but the enzymes are present in all varieties of barley whether they are of winter (two or six rows) or spring.

The malt was ground in a vibrating feeder L 24 from the company Fritsch (Germany).

The various products used for electrophoresis buffers and gels come from the suppliers Alfa Aesar, Carbo Erba and Sigma. The 40% acrylamide comes from Fisher Scientific.

The colorimetric determination of the proteins was carried out with the BC Assay kit from Uptima Interchim.

The ion exchange chromatographs were performed on FPLC Akta explorer 100 and Akta Prime (GE Healthcare, USA) with XK 26/10 columns and Sepharose SP Fast Flow (FF) 50 ml gels and Sepharose DEAE FF (GE Healthcare, USA). Separation is also feasible on other types of cation and anion exchange columns.

The filtration gels were performed on FPLC Akta explorer 10 (Amersham Pharmacia Biotech) and Akta explorer 100 (GE Healthcare, USA) with Sephadex HR (High Resolution) S200 (16/60) and Superose 12 (10/30) columns.

Protein detection was performed by 3-wavelength spectroscopy: at 215, 260 and 280 nm.

HPLC analyzes were carried out on an Alliance Waters 2795 separation module/Waters 2487 dual λ absorbance detector and the column used was a Luna 5μ (C18) 100 Å (250×4.60 mm) (Phenomenex). Detection of the proteins was carried out by 2-wavelength spectroscopy: at 214 and 280 nm.

The samples were analyzed by mass spectrometry, after tryptic hydrolysis, on nano LC-MS/MS ESI ORBITRAP Velos. The peptide analyses were carried out using the Mascot 2.2 software.

The modeling of the enzymes was carried out using the Modeller 9.14 software.

The centrifuge is a Beckman Avanti (USA) J26 XP (rotor: FiberLite® F10BCI-6x500y).

The cloudiness was measured on a Pfeuffer tannometer (Germany) after passing through a Hubert Variostat CC immersion cryothermostat. The non-stabilized control beer is Fink'bräu (Lidl) and the positive control is Brewers Clarex® (DSM, The Netherlands).

The gliadins (total) and the β-lactoglobulins used for the hydrolysis tests were supplied and purified by the INRA of Nantes (BIA center Angers-Nantes/Loire Atlantique).

The peptide Z-GP-pNA and the peptide Z-FR-pNA originate from the company Bachem (Switzerland).

The OD was read by an Epoch plate reader (Biotek, USA).

The dialysis membranes were visking membranes (Medicell Int.) with a cutoff threshold of 12-14000 Da.

Preparation of Buffers

The 0.1M citrate buffer pH 4.3 was prepared with 0.1M citric acid (MW=210.14 g/mol $L^{-1}$) and adjusted to pH 4.3 by the addition of citrate sodium to 0.1 M (MW=294.1 g/mol $L^{-1}$). For the other citrate buffers used, they were also prepared with the solutions at the indicated molarity and adjusted to the desired pH by addition of sodium citrate.

The 50 mM acetate buffer pH 4 was prepared with 50 mM acetic acid and adjusted to pH 4 by the addition of 50 mM sodium acetate (MW=136.08 g/mol $L^{-1}$).

The 50 mM Tris/HCl pH 7.5 buffer was prepared with 50 mM Tris and adjusted to pH 7.5 by the addition of hydrochloric acid (HCl).

The citric acid buffer 0.1 M/disodium phosphate 0.2 M (MW=177.99 g/mol $L^{-1}$) was prepared with 0.1M citric acid and adjusted to pH 4 (or 5) by the addition of 0.2M disodium phosphate.

The buffer for the lyophilization test was prepared with 100 mM Tris/HCl pH 8.5 (PM T5ris=121.14 g/mol $L^{-1}$) to which was added EDTA (Ethylene diamine tetra acetic 5 mM (MW=292.24 g/mol $L^{-1}$), 2 mM cysteine (MW=121.2 g/mol $L^{-1}$), 4% mannitol (w/v) and 1% sucrose (w/v).

Preparation of the Extract

Figure 1:
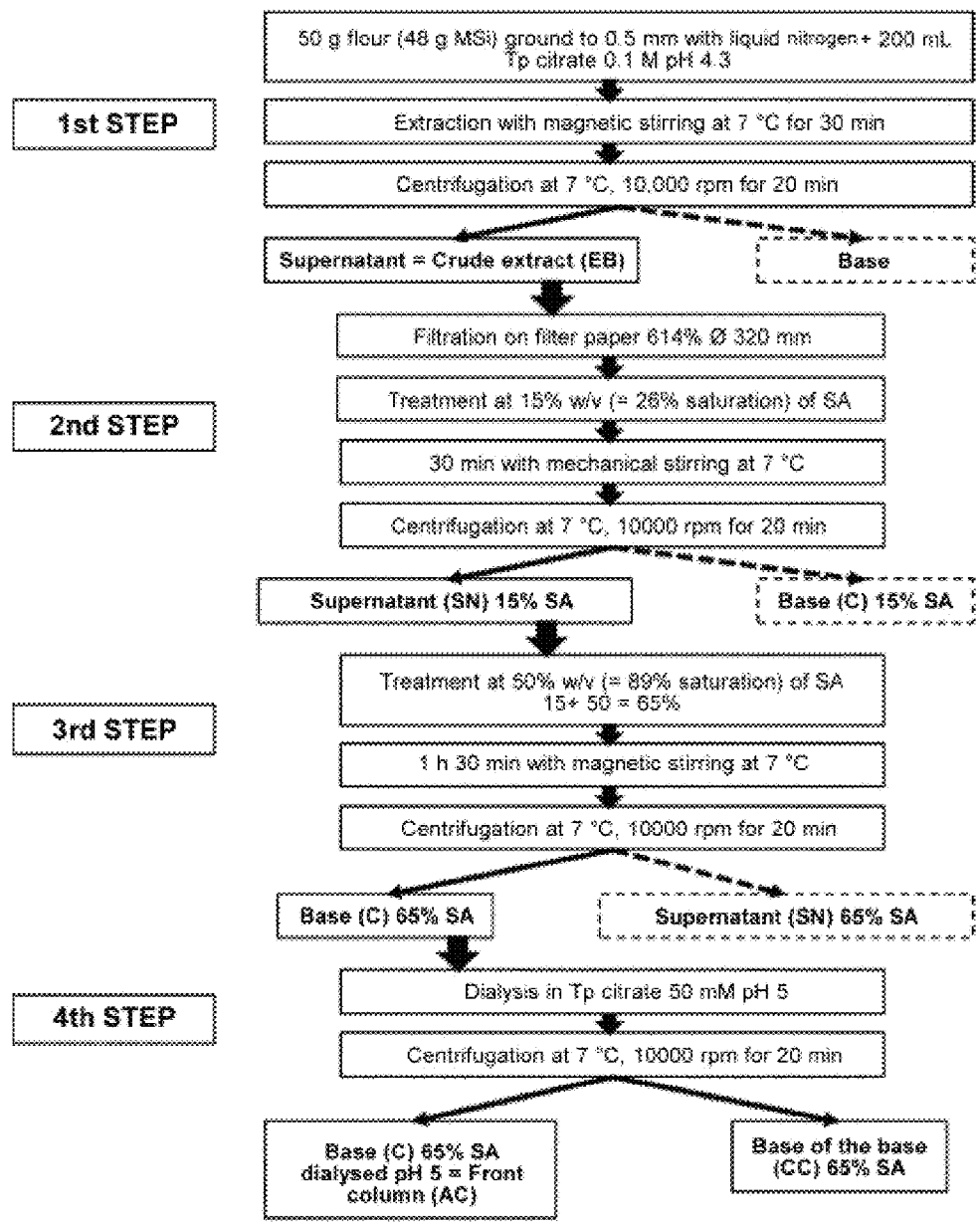
FIG. 1: Overview of the protocol for obtaining the extracts of barley malt used in Example 3.

The malt grains were ground under liquid nitrogen to 0.5 mm. 48 g of MSi (Initial Dry Material) flour were suspended in 200 mL of 0.1 M citrate buffer pH 4.3 with magnetic stirring at 7° C. for 30 minutes. After centrifugation at 10,000 rpm, for 20 minutes at 7° C., the supernatant was recovered and filtered on filter paper. It is referred to as "crude extract" (EB). This EB was treated with 26% saturation with ammonium sulphate $((NH_4)_2SO_4)$ (SA) or 15% w/v with magnetic stirring at 7° C. for 30 minutes. This followed a second centrifugation at 10,000 rpm for 20 minutes at 7° C. The supernatant was recovered and filtered on filter paper. Thus, the "supernatant treated with 15% ammonium sulfate" (SN-15%-SA) was obtained. SA was added to the SN-15%-SA so as to reach 89% saturation or 65% w/v final. After 1 hour 30 minutes at 7° C. with magnetic stirring at 7° C., the extract was centrifuged again at 10 000 rpm for 20 minutes at 7° C. The supernatant was removed and the base obtained was resuspended in 50 mL of 0.1 M citrate buffer pH 4.3 and dialysed first of all for 30 minutes in 2 L of distilled water followed by two baths of 2 h each in 2 L of 50 mM citrate buffer pH 5 and then overnight against 5 L of 50 mM citrate buffer pH 5 in order to obtain the final extract called C65% SA dia pH 5 (base 65% dialysed ammonium sulphate pH 5) which is also the "forward column" (AC) for passage on the SP Sepharose FF (FIG. 1).

Chapon Test

All the efficacy tests for reducing the turbidity of the beer were carried out via the Chapon test (Chapon (1993) J. Inst, Brew 99: 49-56). 2 mL of sample were mixed with 25 mL qs of non-stabilized beer and then incubated at 37° C. for a minimum of 5 h in a water bath. In polystyrene test tubes, 9.4 mL of incubated sample was taken and 0.6 mL of 96% ethanol was added. The tests were carried out in duplicate. After incubation for 30 min at −8° C. in a cryostat bath, the turbidity was measured at −8° C. on a Pfeuffer tannometer. The results are expressed in EBC (European Brewery Convention) (0.25 EBC=1 NTU (Nephelos Turbidity Unit)).

Ion Exchange Chromatographies

Cation exchange chromatography—In a first step, the extract (C65% SA dialyzed at pH 5) was placed on a column (XK 26/10) Sepharose SP FF equilibrated in 50 mM citrate buffer pH 5 (=tp A), flow=13 ml/min (147 cm/h). Elution was carried out by increasing the ionic strength by a linear gradient from 0 to 50% of Buffer B (tp A+1 M NaCl) in 25 CV (column volume). After a plateau at 50% of B for 2 CV, the column was rinsed at 100% B in 7 CV and then rebalanced in buffer A. 15 ml fractions were collected. Only the "non-retained" fraction active in the Chapon test was recovered (NR SP).

Anion Exchange Chromatography

After dialysis twice 2 h and then 1 night in 5 L baths of 50 mM Tris buffer, pH 7.5 (=tp A2), the NR SP was deposited on a DEAE FF Sepharose column, equilibrated by buffer A2, flow rate=5 ml/min and elution was carried out by a linear gradient of 0 to 30% B2 buffer (50 mM Tris pH 7.5+1 M NaCl) over 80 min, followed by a stage of 10 min at 30% and a stage of 20 min at 100% of buffer B2. The collected fractions were 2 mL.

Gel Filtration

Column Sephadex S200—5 mL (4.4 mg of proteins) of the SP/DEAE fraction containing EP-B was deposited on the Sephadex S200 column. The flow rate was 0.5 mL/min and the buffer used was 50 mM citrate buffer pH 4.5. The collected fractions were 5 mL.

Column Superose 12—1.5 mL (1.75 mg protein) of the SP/DEAE fraction containing EP-A was deposited on the Sephadex S200 column. The fraction was previously concentrated on an Amicon Ultra 10 KDa cell of 0.5 mL (Millipore, Ireland). The flow rate was 0.8 mL/min and the buffer used was 50 mM citrate buffer pH 4.5. The collected fractions were 2 mL.

Electrophoresis (SDS-PAGE, PAGE, Zymograms, Tricine)

SDS-PAGE. The different samples were analyzed in SDS-PAGE with a 12% acrylamide separation gel and a 5% concentration gel according to the Laemmli technique (Laemmli (1970) Nature 227: 680-685). The migration was carried out at ambient temperature in an Atto vertical electrophoresis cell under 10 mA in the concentration gel and then 20 mA in the separation gel. Depending on the gels, the colors were made with either Coomassie R250 blue or Coomassie G250 blue. In the wells, 5 μL of known molecular weight standards and 20 μL of sample were deposited. The samples were prepared as follows: 40 μL of sample+20 μL of denaturation solution (50 mM Tris pH 6.8, 20% glycerol, 4% SDS, 0.01% bromophenol blue)+3 μL of β-mercapto-ethanol.

Native PAGE—The protocol was the same as for PAGE gels except for the presence of SDS.

SDS-Tricine PAGE—The SDS-tricine PAGE was performed according to the protocol of Schägger and von Jagow (1987) Anal. Biochem. 166: 368-379, on 10% acrylamide gels for separation before analysis of the bands by mass spectrometry, or 16% for the study of the hydrolysis of the hordeins. The gels were stained with Coomassie G250 blue.

Zymograms—The zymograms were performed on 12% PAGE gels in which 0.1% gliadins was incorporated according to the protocol of Prabucka and Bielawski (2004) Acta Physiol. Plant. 26: 383-391. Before staining with Coomassie R 250 blue, the gel was rinsed twice for 1 hour in 0.1 M citrate buffer pH 4.3 and then incubated in 0.1 M citrate buffer pH 4.3/4 mM cysteine 40° C. overnight.

Analysis in Mass Spectrometry

After SDS-Tricine-PAGE and staining with Coomassie G250 blue, the bands of interest were cut with a cutter under sterile conditions and then analyzed by the BIBS platform of the INRA of Nantes (http://www.bibs.inra.com).

Hydrolysis of Hordeins, Gliadins and β-Lactoglobulins

Hydrolysis of the hordeins: extraction—25 g of flour of barley grains ground to 0.5 mm were mixed with magnetic stirring with 200 ml of 0.5 M NaCl for 1 hour at room temperature. The mixture was then centrifuged at 10,000 rpm for 30 minutes at 12° C. The supernatant was removed and the base was suspended in 200 ml of 0.5 M NaCl and stirred for 1 h at room temperature. After being centrifuged at 10,000 rpm for 30 minutes at 12° C., the supernatant was removed and the base was frozen at −20° C. and then lyophilized.

The lyophilisate was resuspended in 50% propanol (15 mL/g) at 60° C. with magnetic stirring for 45 min and then centrifuged at 10,000 rpm for 30 minutes at 12° C. The supernatant called "supernatant propanol" was stored at 4° C. and the base was extracted again with 50% propanol.

The base was then suspended in 50% propanol (15 mL/g)+2% of β-mercaptoethanol (βME) at 60° C. with magnetic stirring for 45 minutes. It was then centrifuged at 10,000 rpm for 30 minutes at 12° C. The supernatant named "supernatant propanol/β-mercaptoethanol" was stored at 4° C. The base underwent this step twice more.

The propanol and propanol/βME supernatants were dialyzed separately against 20 L of distilled water (3 baths of 2 h and overnight) and then centrifuged at 10,000 rpm for 30 minutes at 12° C.

The bases as well as the supernatants were frozen at −20° C. and then lyophilized. The lyophilisates were then ground to a fine powder and stored at −20° C.

At the end of the extraction, Propanol (H) and Propanol/β-mercaptoethanol Hordeins (HPβME) were obtained (Koehler and Ho (1990) Plant Physiol. Inst Brew 98: 471-478, Zhang and Jones (1996) Planta 199: 565-572).

Since these extracts were difficult to dissolve, they were delipidated before analysis. The HP were delipidized according to the following protocol: in a 15 mL glass tube, 0.302 g of HP were weighed and suspended in 10 mL of dichloromethane+5 mL of acetone. After vortexing for 20 minutes and centrifuging at 4° C. for 10 minutes at 3000 rpm, the supernatant was removed and the base was treated a second time and then dried under vacuum and stored at −20° C. The extract obtained is called HPdl.

Hydrolysis of hordeins: SDS-PAGE and HPLC analysis—After suspending the hordeins (HPdl) (1 mg/mL) in 20 mM sodium-succinate buffer pH 4.5 containing 10 mM β-mercaptoethanol, 2 μg of proteins were added for the fraction containing EP-B as well as for the positive control (Brewer Clarex®). Incubation was carried out at 40° C. 20 μL of the reaction mixture were taken at different times (T=0/5/15/30/60/90 min/2 h/4 h and 24 h), diluted in the denaturation buffer, boiled to stop the reaction and then frozen at −20° C. before analysis on an SDS-Tricine-PAGE 16% gel. In the case of the analysis by reversed phase HPLC, 100 μl of the 24 h extract were taken.

Hydrolysis of Gliadins and β-Lactoglobulin: Reverse-Phase HPLC Analysis. In the case of gliadins and β-lactoglobulin, a 1 mg/mL solution was prepared in 50 mM acetate buffer pH 4. Tests were also carried out by adding DL-Dithiothreitol (DTT) to a final concentration of 2 mM prior to incubation. To initiate the hydrolysis reaction, 2 and 5 μg of proteins (EP-B/EP-A and BC) were added in 200 μL of substrate+/−4 μL of 0.1 M DTT. The reaction mixture incubated at 40° C. for 20 h.

HPLC (High Performance Liquid Chromatography) Reverse Phase

The Luna C18 column (Phenomenex) was equilibrated by eluent A (H$_2$O milliQ+trifluoroacetic acid (TFA) 0.11%) and elution was carried out by a linear gradient of 0 to 50% eluent B (acetonitrile+0.09% TFA) in 54 min at a flow rate of 1 mL/min for the hydrolysis of gliadins and β-lactoglobulins and a linear gradient from 0 to 60% B in 32 min at a flow rate of 0.8 mL/min for hydrolysis of the hordeins.

50 μL of sample were injected. The reading was made at 214 nm and 280 nm and the column temperature was maintained at 50° C. (Marchylo and Kruger (1984) Cereal Chem., 61: 295-301, Marchylo et al., (1986) Cereal Chem. 63: 219-231).

Hydrolysis of Z-Gly-Pro-pNA and Z-Phe-Arg-pNA Peptides

For each peptide tested, hydrolysis was carried out at pH 4 and pH 5 (Davy et al., (1998) Plant Physiol., 117: 255-261, Simpson et al., (2001) Plant Sci 161: 825-838).

Hydrolysis of the Z-Gly-Pro-pNA Peptide (Z-GP-pNA)—17.6 μg of proteins were reacted for each enzyme, EP-A, EP-B and BC with qsp 500 μL of acid buffer 0.1 M citric acid/0.2 M disodium phosphate (pH 4 or 5) and 125 μL of 10 mM substrate (solubilized in the same buffer+40% dioxane). The final concentration for the Reaction Volume (VR) in substrate was therefore 2 mM and 8% dioxane.

For each sample, the hydrolysis was done in duplicate (deposition of 250 μL of the VR in a microplate of 96 wells).

The release of the pNA was followed by reading the OD at 410 nm at different times (T=0/10/20/30/40/50/60 min and 1 h30/2 h/2 h30/3 h/3 h30/4 h/4 h30/5 h/5 h30/6 h and 24 h).

Hydrolysis of the Z-Phe-Arg-pNA Peptide (Z-FR-pNA)—17.6 μg of proteins were reacted for each enzyme, EP-A, EP-B and BC, with qsp 500 μL of acetate buffer 50 mM (pH 4 or 5)+5% DMSO and 125 μL of 10 mM substrate solubilized in the same buffer. The final concentration for the reaction volume (VR) in substrate was therefore 2 mM.

For each sample, the hydrolysis was done in duplicate (deposition of 250 μL of the VR in a microplate of 96 wells).

The release of the pNA was monitored by reading the OD at 410 nm at different times (T=0/10/20/30/40/50/60 min and 1 h30/2 h/2 h30/3 h/3 h30/4 h/4 h30/5 h/5 h30/6 h and 24 h).

Freeze-Drying Test

After passing the SP then DEAE columns of the malt extract, the fractions corresponding to the separation peak of the enzyme EP-B were combined. The final volume obtained was divided into two and then separately dialyzed for 30 minutes in distilled water followed by two 2 h baths and then overnight at 4° C. in 50 mM citrate buffer, pH 4.2, for the one and in Tris/HCl/EDTA/Cysteine/Mannitol/Sucrose for the other.

The volume after dialysis was again divided into two. The first portion was stored at −20° C. awaiting analysis in the Chapon test and the second was freeze-dried. The lyophilisate was suspended in a volume of distilled water equal to the initial volume placed on the lyophilizer and was analyzed in the Chapon test.

Results

Figure 2:
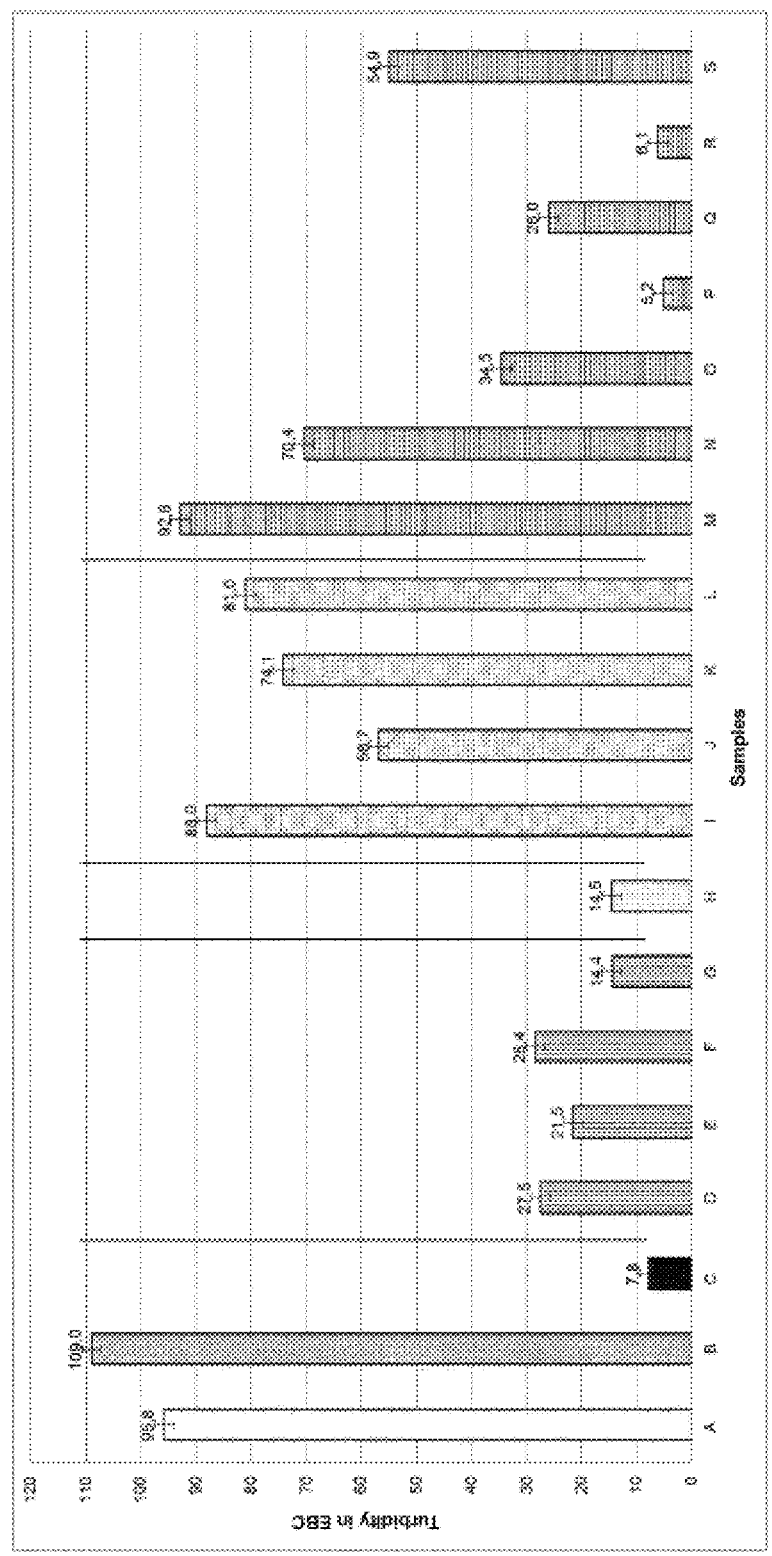
FIG. 2: Effect on the colloidal cloudiness of the beer (Chapon test) of the extracts and fractions obtained in Example 3. A: Negative control (1 mL of Tp citrate 0.1 M pH 4.3+1 mL Tp Tris 50 mM pH 7.5); B: Negative control (1 mL Tp citrate 50 mM pH 5); C: Positive control (190 µL of Brewers Clarex® diluted 1/25+1 mL Tp Citrate 0.1 M pH 4.3); D: crude extract (EB); E: supernatant 15% SA pH 4.3; F: C 65% SA dia (Tp citrate 50 mM pH 5); G: not retained (NR) on cation exchange column (SP); H: front DEAE column (NR SP dia pH 7.5); I: NR DEAE 42-82; J: NR DEAE 83-95; K: NR DEAE 96-150: L: NR DEAE 151-end; M: fraction 16; N: fraction 21: O: fraction 25; P: fraction 31; Q: fraction 38; R: fraction 46; S: fraction 55.

Comparison in Chapon Test of the Efficacy of the Extracts Obtained at Each Stage of the Enzyme Extraction of Barley Malt By measuring the decrease of the cloudiness, the Chapon test allows the selection of the active fractions during the purification. Thus, after fractionation with ammonium sulfate, the inventors showed that the activity was conserved in the dialysed SN15% SA and then in the dialysed C65% SA (FIG. 2). The dialysed C15% SA and the dialysed SN65% SA have no activity. A Chapon test performed by adding equivalent amounts of proteins (1 mg) showed a strong increase in activity in the C65% SA dia (108 EBC for EB, 50.2 EBC for C65% SA dia). Thus, the ammonium sulfate treatment allows a first concentration and purification of the enzymes of interest.

Separation of Enzymes from Barley Malt by Ion Exchange Chromatography

The analysis by the Chapon test of the fractions eluted after chromatography of the malt extract (C65% SA dialyzed with pH 5) on a cation exchange column (SP) showed that the enzymatic activity was in the fraction not retained on the column. This fraction was then separated on an anion exchange column (DEAE). This second chromatography made it possible to isolate two enzymatic fractions capable of reducing the turbidity of the beer at 5.2 and 6.1 EBC (FIG. 2 fractions 31 and 46).

Analysis by Electrophoresis (SDS-PAGE, PAGE, Zymograms)

Analysis by electrophoresis showed that fraction 31 was composed of several protein bands including a main group at about 35 kDa, a band at about 60 kDa, and a thinner band at around 30 kDa. Fraction 46 contained 2 bands of PM at about 60 and 35 kDa. The zymogram confirmed the presence in fractions 31 and 46/47 of enzymes capable of hydrolyzing proteins rich in prolines (gliadins). The enzymes in these two fractions had different mobilities indicating that they were different.

Separation of Enzymes from Barley Malt by Gel Filtration

After separating the enzymes of interest from barley malt by ion-exchange chromatography, the inventors used gel filtration chromatography in order to refine the purity of the fractions exhibiting the enzymatic activity. Separation of fraction 31 on the Sephadex S200 column showed a main peak preceded by two shoulders. Chapon and zymogram analysis revealed that the enzyme was present in the 1C4 fraction corresponding to the main peak. By SDS electrophoresis, the inventors found that this fraction consisted of several protein bands in the region of 35 kDa.

The chromatogram of fraction 47 showed several poorly separated peaks. The Chapon and zymogram analysis revealed that the enzyme was present in the 5A5 fraction corresponding to the first peak.

Characterization of Enzymes by Mass Spectrometry

After SDS-PAGE, the protein bands of fractions 31 and 46 were cut out and analyzed by mass spectrometry after tryptic hydrolysis. In the case of fraction 31, the 2 bands of PM 30 kDa and 28 kDa correspond to the mature form of a cysteine protease: EP-B (Reference Uniprot: P25249 (SEQ ID NO: 3) or P25250: 4)). Two variants of this protease have been described but the differences between these two variants are too small for the analysis to indicate which variant is present. EP-B P25249 and P25250 are proteases of PM 25180 and 25318 and pI 4.77 and 4.96. Fraction 31 also contains β-amylases (PM band 60,000) and serpins (group of bands around 35,000).

In the case of fraction 46, cysteine protease was also found in 2 bands of PM 30 and 28 kDa which correspond to the mature form of cysteine protease EP-A (Uniprot reference: 004675 (SEQ ID NO: 1) or 004677 (SEQ ID NO: 2)). As for EP-B, two variants exist but the analysis does not make it possible to say which variant is present. Based on the mature protein sequences, these proteases had respective PMs of 25590 and 25648 and pIs of 4.4 and 4.37. The other bands observed on the electrophoregram also correspond to a β-amylase and serpins.

Sequence alignment showed that the sequences of the two EP-Bs and those of the two EP-As showed 98% and 99% identical amino acids, respectively. In contrast, EP-A had 52% sequential homology with EP-B. These two cysteine proteinases have a similar structure and have an identical catalytic site composed of three amino acids: cysteine (28), aspartate (162) and histidine (163). Although they have a similar effect on decreased beer cloudiness compared to the positive control enzyme (Brewers Clarex®), they are no less different. Indeed, they have only 9 and 11% (respectively) of identical amino acids with Brewers Clarex®. Moreover, the large number of gaps required for this alignment shows that these enzymes have no structural kinship. This lack of structural homology may also be demonstrated with the 3D modeling of the enzyme.

Hydrolysis of Hordeins, Gliadins and β-Lactoglobulins

Electrophoresis analysis of hydrolysis of hordeins— Monitoring of hydrolysis of hordeins by SDS-Tricine-PAGE gel analysis did not allow us to conclude whether there was a real difference in mechanism of action between EP-B and positive control, although EP-B appears to be more effective. Indeed, there are no more bands visible after 24 h of reaction whereas bands may still be observed after 24 h in the presence of Brewers Clarex®.

HPLC analysis of horde hydrolysis—The fraction enriched in EP-B (fraction 31) is capable of hydrolyzing the hordeins and degrades them differently from the positive control (Brewers Clarex®). Indeed, the chromatograms showed that some peptides generated were different.

Figure 3:
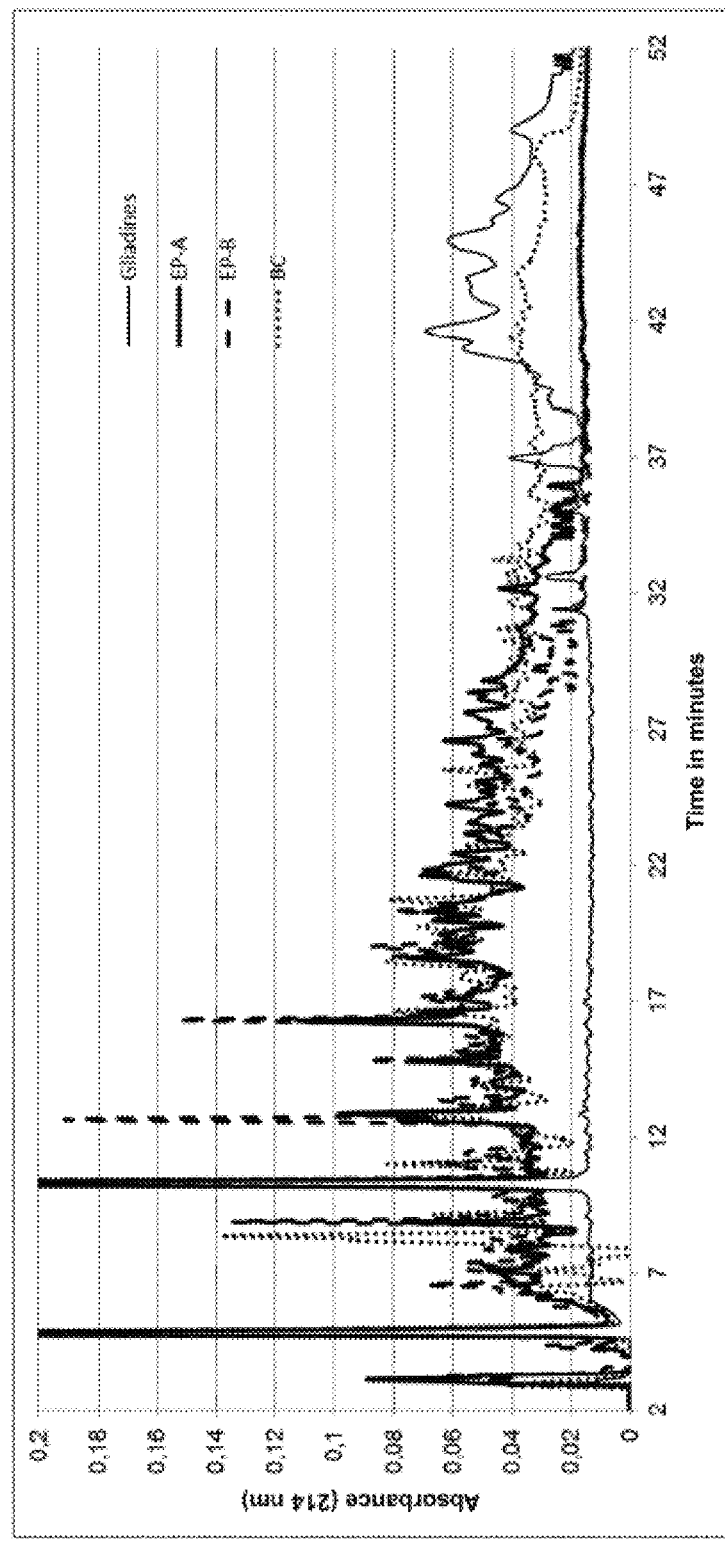
FIG. 3: Chromatogram of the hydrolysis of gliadins with DTT by the enzymes of barley malt and Brewers Clarex® in HPLC on Luna C18 described in Example 3.

HPLC analysis of gliadin hydrolysis—In the case of gliadins, chromatograms showed a different action between barley malt enzymes (EP-B and EP-A) and the positive control (Brewers Clarex®). It was found that hydrolysis (in the presence of DTT) by cysteine proteinases is complete, unlike that with Brewers Clarex (BC). Very many hydrophilic peptides have been generated by the hydrolysis by the different enzymes making it difficult to compare the chromatograms. We may still see some differences between the Brewers Clarex and the two proteases of barley malt and between the two proteases (FIG. 3).

Figure 4:
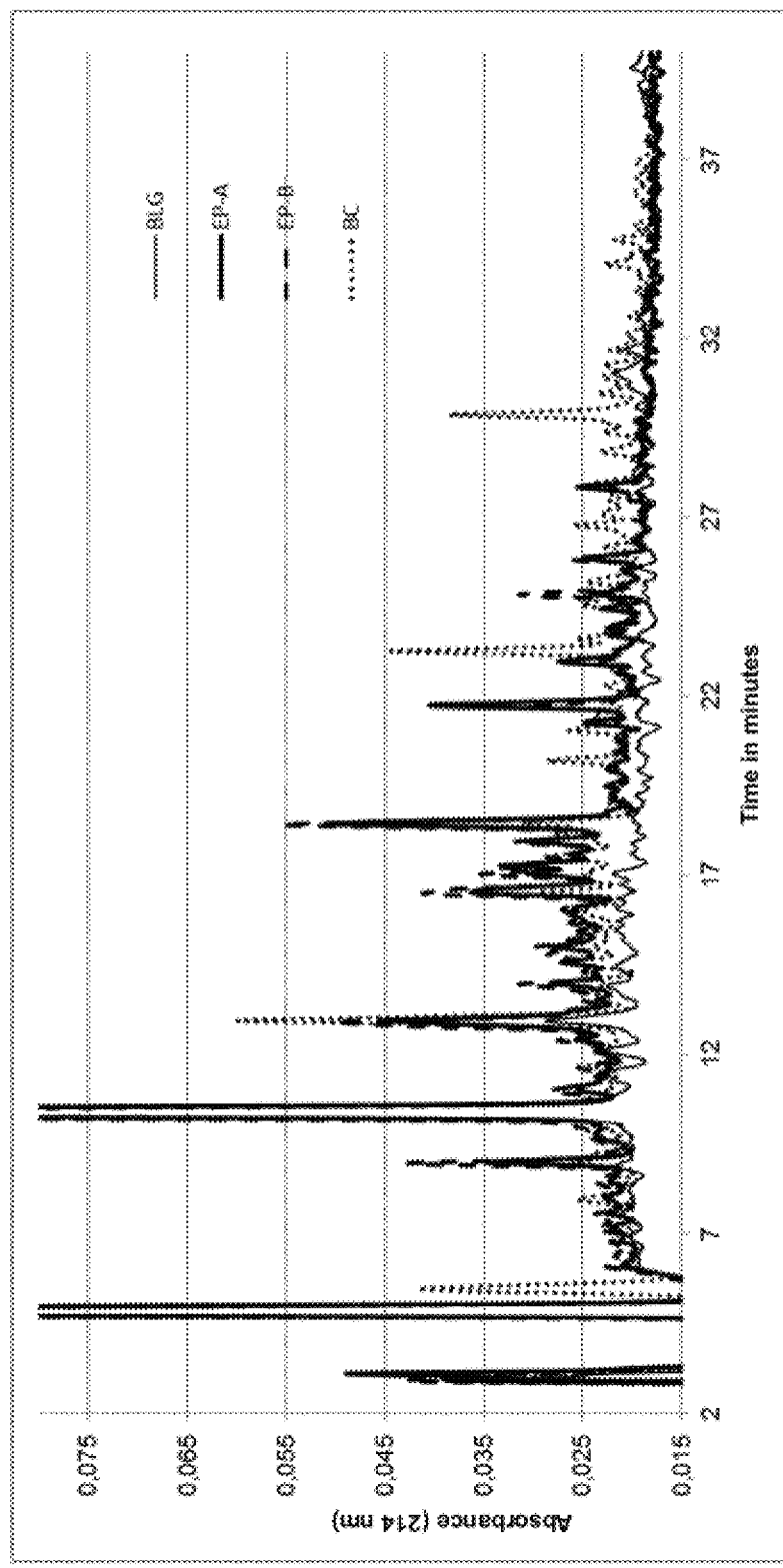
FIG. 4: Enlargement of a chromatogram of the hydrolysis of β-lactoglobulins with DTT by the enzymes of barley malt and the Brewers Clarex® in HPLC on Luna C18 described in Example 3.

HPLC analysis of β-lactoglobulin hydrolysis—In the case of hydrolysis of β-lactoglobulins, chromatograms also showed a different action between the enzymes of barley malt (EP-B and EP-A) and the positive control (Brewers Clarex®). This difference is visible with or without DTT (FIG. 4).

Figure 5:
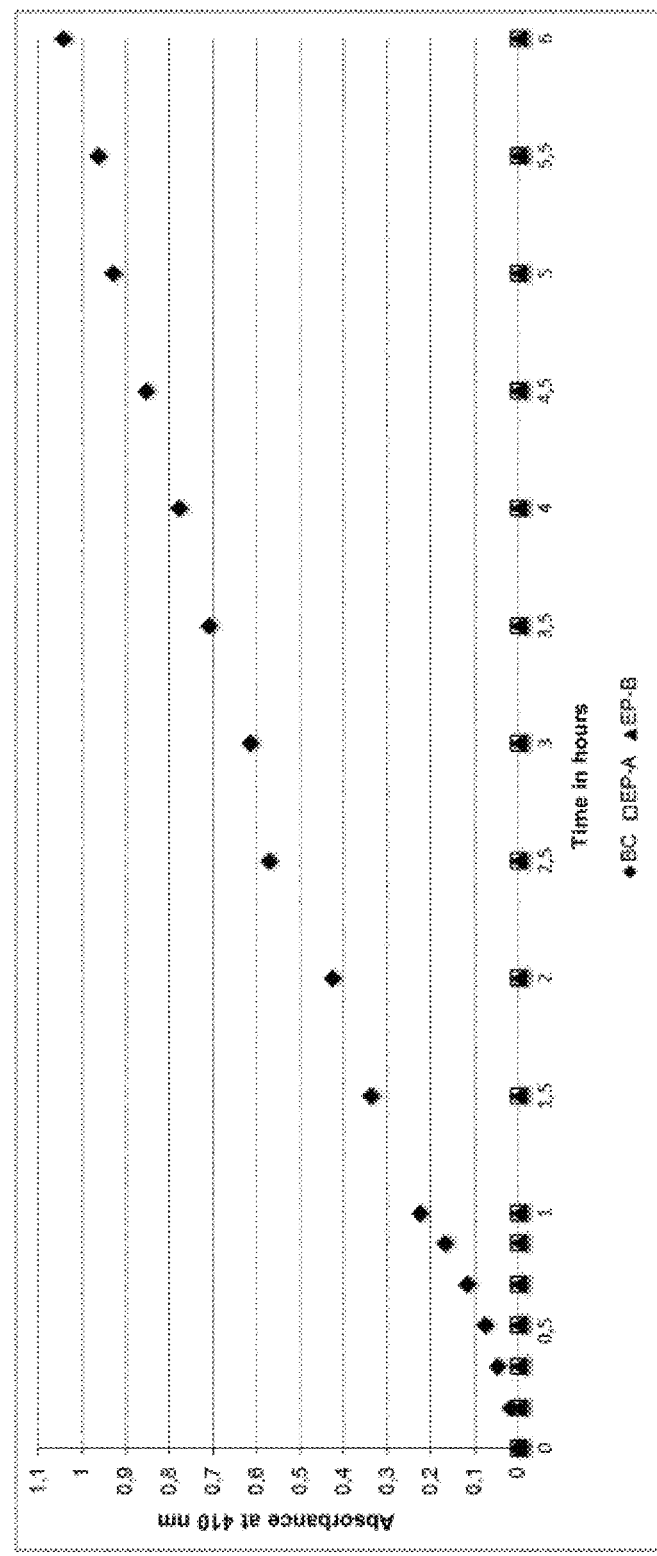
FIG. 5: Kinetics over 6 h of the hydrolysis of the peptide Z-Gly-Pro-pNA by the enzymes of barley malt and the Brewers Clarex® at pH 4 described in Example 3.
Figure 6:
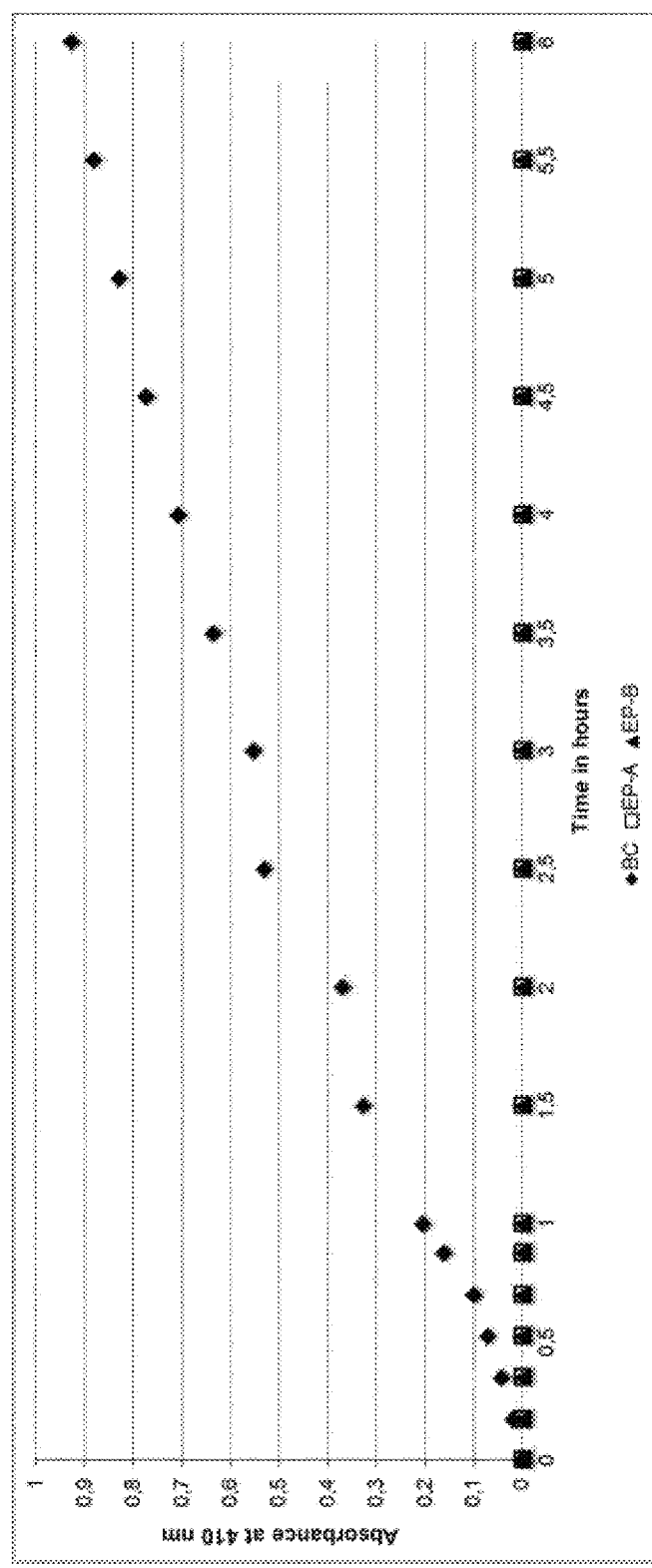
FIG. 6: Kinetics over 6 h of the hydrolysis of the Z-Gly-Pro-pNA peptide by the enzymes of barley malt and the Brewers Clarex® at pH 5 described in Example 3.

Hydrolysis of Z-Gly-Pro-pNA and Z-Phe-Arg-pNA Peptides Hydrolysis of Z-Gly-Pro-pNA Peptide—Only Brewers Clarex® was capable of hydrolyzing the Z-GP-pNA peptide in the tests performed (FIGS. 5 and 6). In addition, Brewers Clarex is equally effective at pH 4 and pH 5. For barley malt enzymes: EP-A and EP-B have zero OD and even after 24 h of incubation, reaction is carried out at pH 4 or 5.

This experiment demonstrates that the site of action of the Brewers Clarex is different from that of the cysteine proteases EP-A and EP-B.

Hydrolysis of the Z-Phe-Arg-pNA Peptide—In the case of the Z-FR-pNA peptide, the hydrolysis is only visible with the EP-B enzyme. There is no degradation with EP-A or Brewers Clarex. In addition, EP-B is more effective at pH 4. Indeed, the OD at pH 5 is half that of pH 4.

Figure 7:
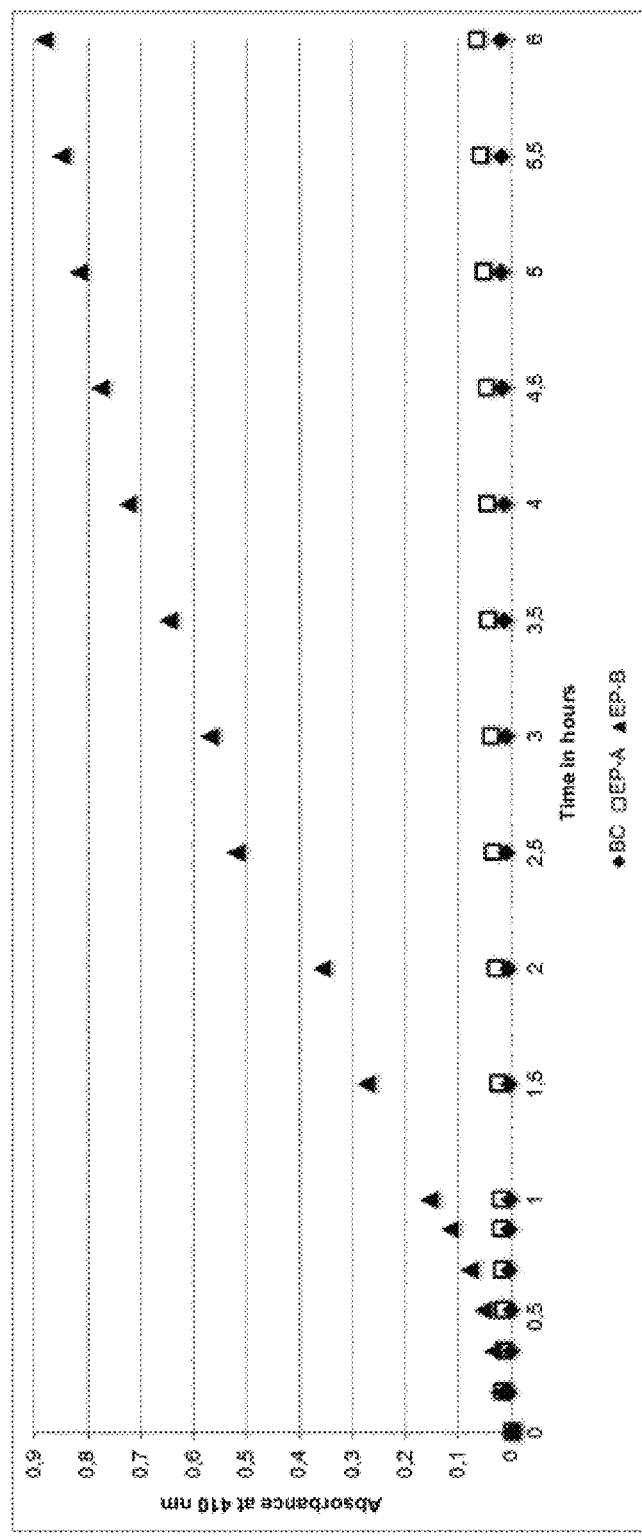
FIG. 7: Kinetics over 6 h of the hydrolysis of the Z-Phe-Arg-pNA peptide by the enzymes of barley malt and the Brewers Clarex® at pH 4 described in Example 3.
Figure 8:
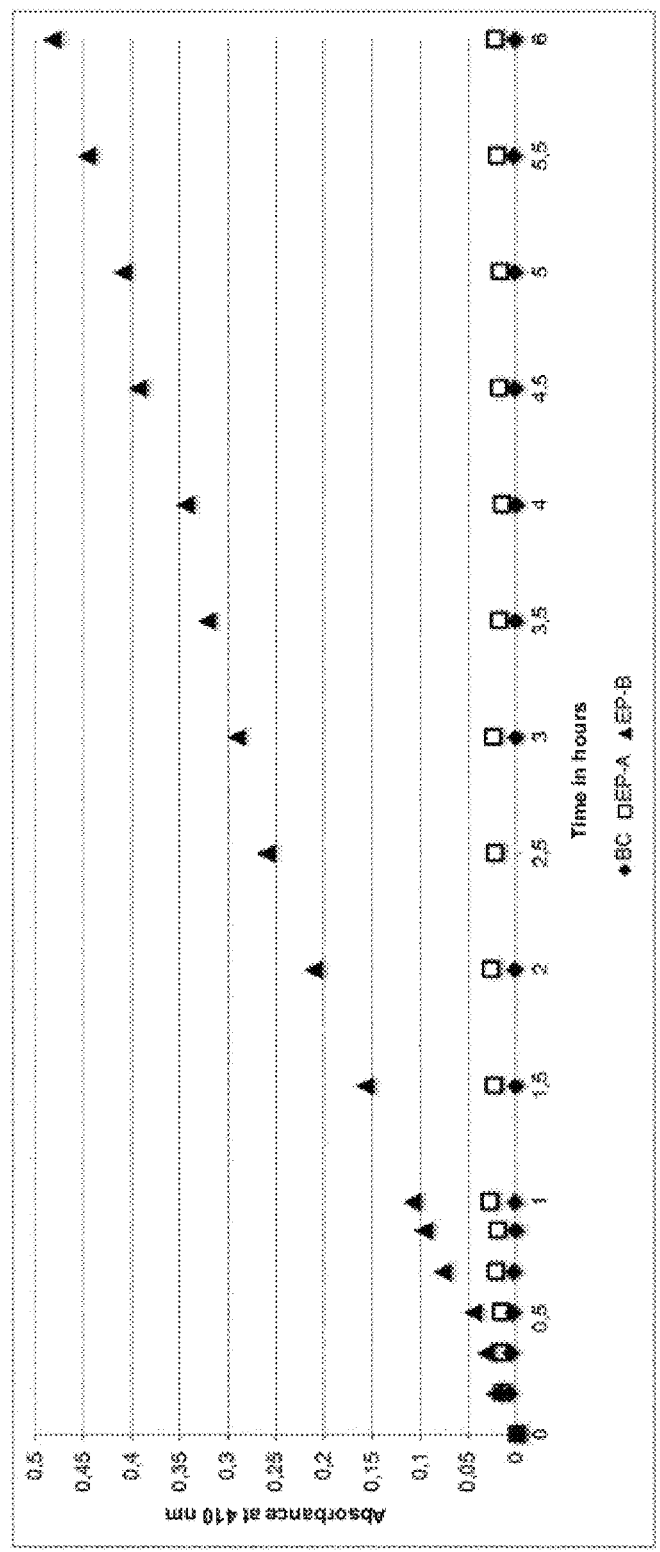
FIG. 8: Kinetics over 6 h of the hydrolysis of the Z-Phe-Arg-pNA peptide by the enzymes of barley malt and the Brewers Clarex® at pH 5 described in Example 3.

This test leads to the conclusion that barley malt enzymes not only have a different breeding site but also differ from Brewers Clarex (FIGS. 7 and 8).

Freeze-Drying Test

The inventors observed that the enzymatic activity was preserved after lyophilization.

The two buffers tested allow the activity to be maintained, but Tris/EDTA/Cysteine/mannitol/sucrose buffer is more effective.

Conclusions

The inventors have shown that two enzymatic fractions isolated from barley malt are capable of reducing the colloidal cloudiness of beer and of hydrolyzing the prolamins of cereals (hordeins and gliadins). These two enzyme fractions are enriched respectively in two proteases EP-B and EP-A, cysteine proteinases of barley. These two enzymes are very similar in terms of their amino acid sequences (primary structure) and their sequences are not at all identical with that of the Brewers Clarex® enzyme. Finally, the hydrolysis of prolamins (hordeins, gliadins) as well as β-lactoglobulin, as well as the hydrolysis of the Z-Gly-Pro-pNA and Z-Phe-Arg-pNA peptides, show that these cysteine proteinases have different specificities (cleavage sites) and are also different from that of the Brewers Clarex® enzyme.

Example 4: Hydrolysis of Gliadins by EP-A, EP-B and Crude Extract of Malt

This example shows that the enzymes EP-A and EP-B cleave the gliadins in a different way, suggesting a synergy in the action of the two enzymes.

Material and Methods

The gliadins are solubilized at 4 mg/ml in 50 mM acetic acid and then diluted to 1 mg/ml with 50 mM sodium acetate buffer at pH 5 and mixed with various extracts. The mixture of gliadins and acetate buffer represents the control T, the mixture of gliadins and crude extract obtained as described in Example 3 is denoted EB, the mixture of gliadins and EP-A obtained as described in Example 3 is denoted EP-A, and the mixture of gliadins and EP-B obtained as described in Example 3 is denoted EP-B. The mixtures are incubated overnight at 37° C. with stirring.

The amounts of enzymes added were calculated in order to obtain a substrate enzyme ratio of 4%. The samples are incubated for 18 hours at 37° C. before being analyzed by high performance liquid chromatography (HPLC).

Reverse Phase HPLC Analysis:

Reverse phase column: Luna, C18, 100A, 5 µm, 250×4.6 mm (Phenomenex)

Eluent A: $H_2O$, TFA 0.11%

Eluent B: Acetonitrile, TFA 0.09%

Flow rate 1 ml/min; spectrophotometer detection at 214 and 280 nm. The 280 nm measurement makes it possible to specifically detect proteins containing aromatic amino acids such as tryptophan. At 214 nm, the signal, although less specific, is about 10 times greater than at 280 nm.

The elution was carried out by a linear gradient of 10 to 60% of eluent B in 20 min. Injection volume: 40 µL. Absorbance is recorded at 214 and 280 nm using a Waters 2487 detector.

Results

Figure 11:
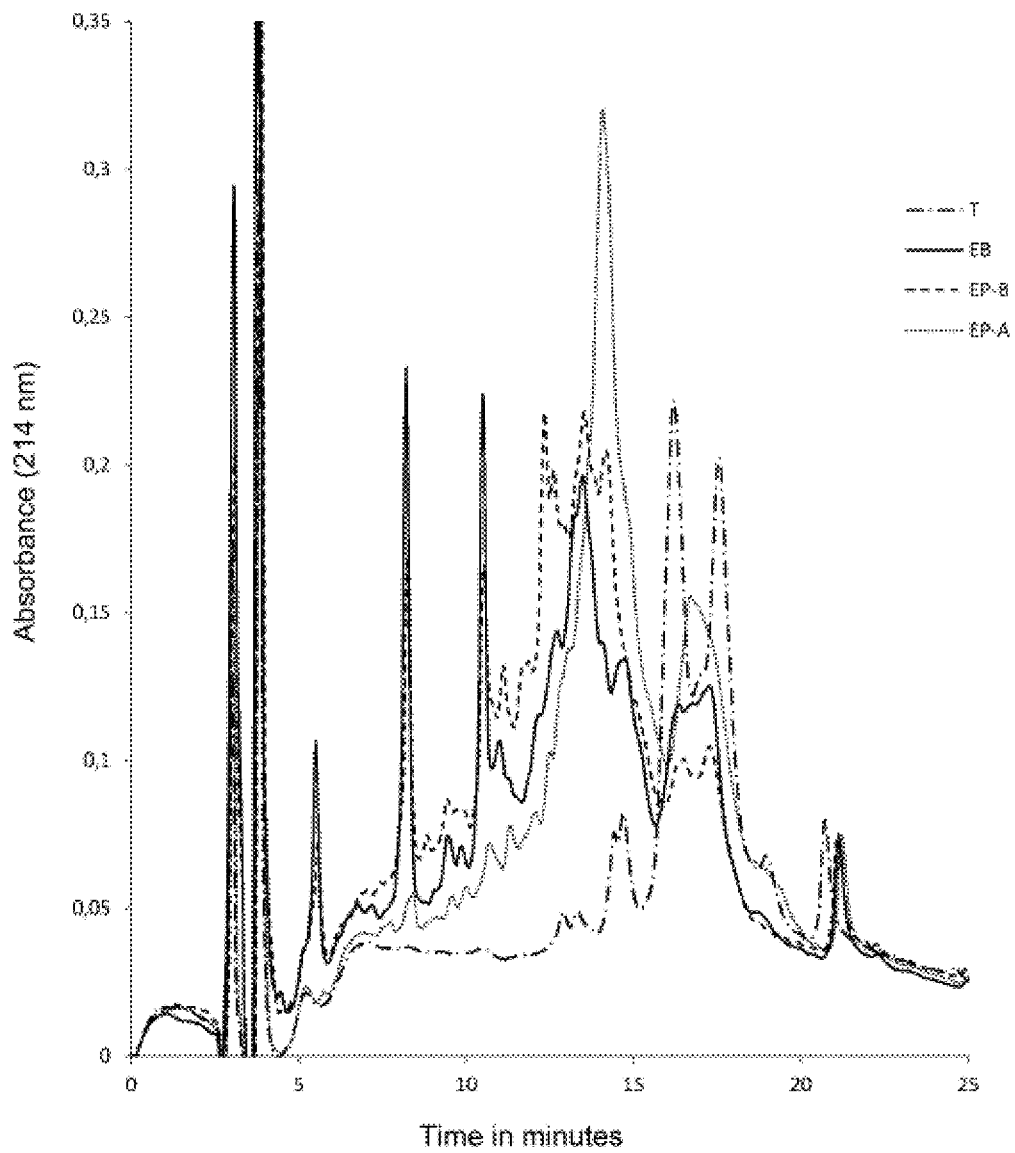
FIG. 11: Chromatogram of the hydrolysis of the gliadins by the enzymes of barley malt and the crude extract of malt in HPLC on Luna C18 described in Example 4. The absorbance is measured at 214 nm.

The hydrolysis tests are carried out on total gliadins. The 2 main peaks corresponding to the gliadins (elution time 16.1 and 17.5 min) show that the gliadins are partially hydrolyzed by the crude extract (EB) and the 2 enzymes. The peaks appearing on the chromatograms after hydrolysis by EP-B and EP-A are different, indicating different cleavage sites (FIG. 11). EP-B hydrolysis is more marked than EP-A, which suggests that smaller peptide chains are released, whereas EP-A allows for more specific hydrolysis, marked by a stronger peak.

Example 5: Fermentation Tests in EBC Tubes ("KIRIN" Type)

This example shows the effect of increasing the fermentation yield of the malt extract according to the invention.

Protocols for the Preparation of Barley Malt Extracts

Grinding of Malt

Malt 2RP Pilsen was stored at 4° C. and then crushed on a ZM 200 mill with a 0.5 mm grid.

Extraction

For each extraction, 900 g of malt are used with 3.6 L of citrate buffer. It lasts 30 min at 7° C. with stirring at 250 rpm. The extracts obtained are centrifuged for 25 min at 8400 rpm and at a temperature of 4° C. with an acceleration and deceleration of 3. The supernatant is recovered and roughly filtered on Marcherey Nagel 614 ¼ 320 mm diameter filters.

Deactivation for Denatured Crude Extract (EBD)

The supernatant is heated without stirring until the first broths appear, and then the supernatant is centrifuged for 25 min at 8400 rpm at a temperature of 4° C. and filtered roughly.

Precipitation 15% (w/v) to Ammonium Sulphate (SA)

The precipitation by the addition of ammonium sulphate is carried out under the same conditions as the extraction, with stirring of 250 rpm and at 7° C. The mixture is centrifuged for 25 min at 8400 rpm and at 4° C. The supernatant is recovered and its volume is measured.

Precipitation 65% (w/v) at SA

The base is recovered in 600 ml of citrate buffer and then filtered roughly before filtration on a 0.45 µm filter. The product obtained is stored at 4° C. awaiting desalting.

Desalination

The desalination is carried out on a Sephadex G25 gel packed in an AxiChrom 70 column (GE Healthcare). The device used is the AKTA Prime Plus (GE Healthcare). The desalination is carried out at ambient temperature and the sample is injected with a flow rate of 40 mL/min. The elution is carried out with 0.1M citrate buffer pH 4.3.

Ion Exchange Chromatography

The gel used is the Sepharose Fast Flow gel, equilibrated with 50 mM citrate buffer pH5, the chromatography is carried out at room temperature. The cysteine endoprotease is in the eluted fraction.

Fermentation Tests

An 11°Plato wort is produced by brewing a "EBC congress" type: heating at 45° C. for 30 minutes, followed by a rise in temperature to 70° C. for 60 minutes, then 210 g of malt are poured for 1260 mL of water.

The different additions (malt extract, controls . . . ) are done before seeding in 770 mL of wort, except the PVPP (40 g/HL), which is added before centrifugation.

The modalities tested respectively correspond to:

T—is a crude extract of barley malt denatured by heat $T_{pvpp}$: no addition

TBC is the positive control with addition of Brewers Clarex®

EB is the crude extract of barley malt

S15 is an extract of malt treated with a solution of 15% ammonium sulphate

S65 is a crude extract treated with 15% ammonium sulfate solution and then the supernatant is treated with a solution of 50% ammonium sulphate 65CH is the modality S65, purified on column SP.

The numbers 1, 2 and 3 correspond to 3 volumes of different additions tested: volumes 1 range from 15 to 30 mL, volumes 2 are 22.5 and 30 mL, volume 3 corresponds to 30 or 37.5 mL.

Seeding:

for fermentations: 720 mL with dry yeast to measure the Apparent Limit Attenuation: 50 mL with dry yeast.

The fermentation/ripening is carried out at a temperature of 13° C. for about 9 days.

The yeast is purged, then the wort is kept cold (about 2° C., minimum 5 days).

At the end of the storage, the fermented worts are centrifuged (centrifugation at 4000 rpm, for 10 minutes) and the supernatant is analyzed.

In order to follow the fermentation, the wort is removed, filtered through kieselguhr, and then a percentage measurement in mass of dry extract of the wort is carried out. This measurement is expressed in degrees Plato (noted °Plato) and implemented by means of an automatic densitometer Anton Paar DMA 35. A monitoring of the yeast population is also carried out.

Results

Figure 12:
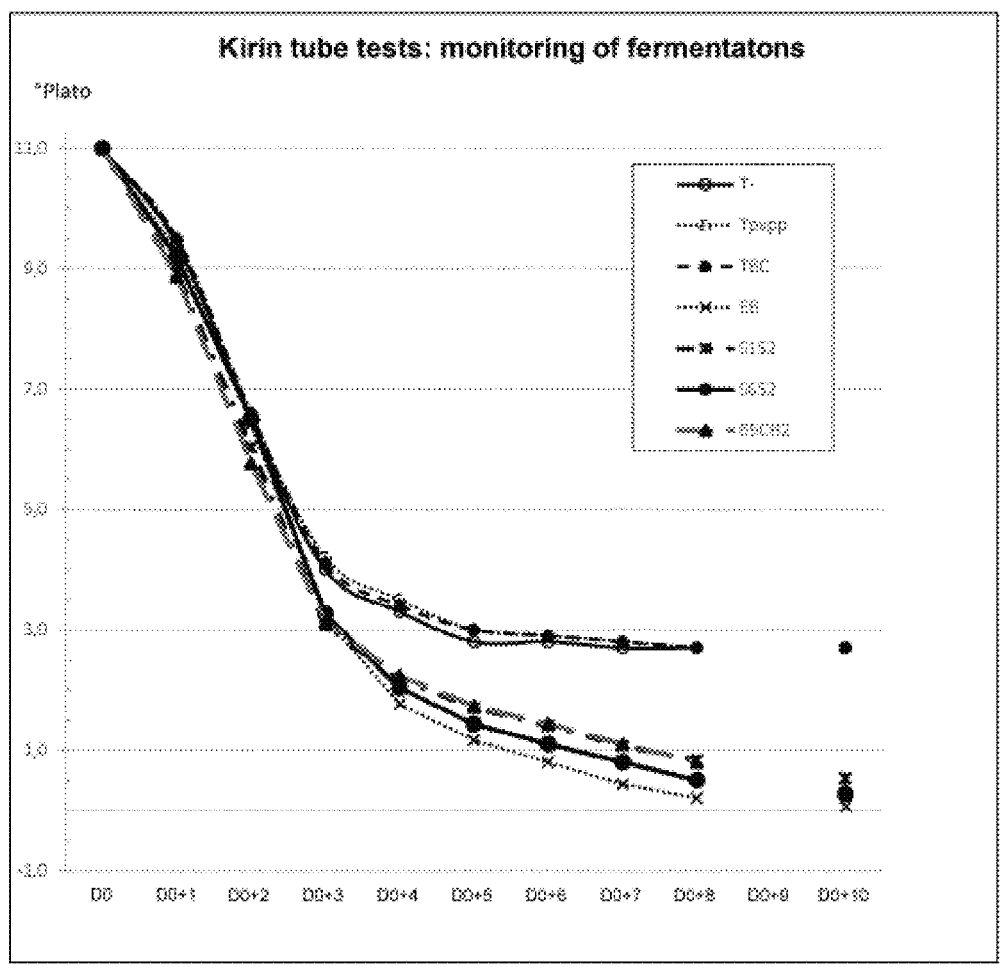
FIG. 12: Effect on fermentation of the malt extract described in Example 5.

Fermentation is accelerated with barley malt extract. At the same time, on D0+3, less fermentable sugars remain in the presence of barley malt than during the fermentation of the control consisting of barley malt alone denatured by heat, negative control and control positive with Brewers Clarex® (FIG. 12).

This application includes a Sequence Listing associated with its image file at the United States Patent Office as follows:

Name of file: P11814US00_NAT_STAGE_SEQUENCE_LISTING

Date of Creation: Oct. 27, 2017

Size of the File in Bytes: 21,666

---

The invention claimed is:

1. A method for preparing a fermented cereal-based beverage with increased fermentation yield, comprising treating said fermented cereal-based beverage during its fermentation by adding cysteine endoprotease or a malt extract comprising cysteine endoprotease.

2. The method according to claim 1, wherein the adding of cysteine endoprotease or of a malt extract comprising cysteine endoprotease is at the beginning of the fermentation of the fermented cereal-based beverage being prepared.

3. The method according to claim 1, wherein the malt extract is a processed malt extract that is obtained by recovery and centrifugation filtration of a crude malt extract.

4. The method according to claim 3, wherein the processed malt extract is treated by differential precipitation with ammonium sulphate.

5. The method according to claim 1, wherein the malt extract is a concentrated malt extract.

6. The method according to claim 1, wherein the fermented cereal-based beverage is beer.

7. The method according to claim 6, wherein the beer is selected from the group consisting of low-fermentation beers, high fermentation beers, beers of single, double or triple fermentation, beers with spontaneous fermentation, beers with mixed fermentation, beers prepared with additives, and beers with a range of alcohol levels from 0 to 10%.

8. The method according to claim 1, wherein cysteine endoprotease is selected from the group consisting of cysteine endoprotease A and cysteine endoprotease B of malt.

9. The method according to claim 1 wherein the malt extract is obtained from green malt or dry malt.

10. The method according to claim 1 wherein the malt extract is made from wheat or barley malt.

11. The method according to claim 1, wherein cysteine endoprotease or the malt extract comprising cysteine endoprotease is added in a sufficient amount so that said fermented cereal-based beverage reaches up to 1°P on the Plato gravity scale 8 days after the start of the fermentation.

12. The method according to claim 11, wherein for the equivalent fermentation time, there are fewer fermentable sugars still present in the fermented cereal-based beverage as compared to an identical amount of an identical fermented cereal-based beverage that has not undergone said treatment.

13. A method of reducing the cloudiness of a fermented cereal-based beverage comprising treating said fermented cereal-based beverage by adding during preparation of said fermented cereal-based beverage a cysteine endoprotease or a malt extract comprising cysteine endoprotease; wherein the cysteine endoprotease or the malt extract comprising cysteine endoprotease is added at any stage of the preparation of the fermented cereal-based beverage and is not followed by destroying the cysteine endoproteasic activity.

14. The method according to claim 13, wherein addition of cysteine endoprotease or a malt extract comprising cysteine endoprotease reduces the cloudiness of the fermented cereal-based beverage by at least 65 EBC units when turbidity is measured at −8° C. as compared to an identical fermented cereal-based beverage that has not undergone said treatment.

15. The method according to claim 13, wherein turbidity is measured using the Chapon test.

16. The method according to claim 13, wherein the malt extract is a processed malt extract that is obtained by recovery and centrifugation filtration of a crude malt extract.

17. The method according to claim 16, wherein the processed malt extract is treated by differential precipitation with ammonium sulphate.

18. The method according to claim 13, wherein the malt extract is a concentrated malt extract.

19. The method according to claim 13, wherein the fermented cereal-based beverage is a beer.

20. The method according to claim 19, wherein the beer is selected from the group consisting of low-fermentation beers, high fermentation beers, beers of single, double or triple fermentation, beers with spontaneous fermentation, beers with mixed fermentation, beers prepared with additives, and beers with a range of alcohol levels from 0 to 10%.

21. The method according to claim 13, wherein cysteine endoprotease is selected from the group consisting of cysteine endoprotease A and cysteine endoprotease B of malt.

22. The method according to claim 13, wherein the malt extract is obtained from green malt or dry malt.

23. The method according to claim 13, wherein the malt extract is made from wheat or barley malt.

24. The method according to claim 13, wherein the cysteine endoprotease or a malt extract comprising cysteine endoprotease is added during the fermentation of the fermented cereal-based beverage.

25. The method according to claim 24, wherein the cysteine endoprotease or a malt extract comprising cysteine endoprotease is added during low fermentation, during high fermentation, or during spontaneous fermentation.

26. The method according to claim 24, wherein the adding of cysteine endoprotease or of a malt extract comprising cysteine endoprotease is at the beginning of the fermentation of the fermented cereal-based beverage being prepared.

27. A method of reducing the cloudiness of a fermented cereal-based beverage and increasing fermentation yield of a fermented cereal-based beverage comprising treating said fermented cereal-based beverage during its fermentation by adding cysteine endoprotease or a malt extract comprising cysteine endoprotease.

28. The method according to claim 27, wherein the adding of a cysteine endoprotease or of a malt extract comprising cysteine endoprotease is at the beginning of the fermentation of the fermented cereal-based beverage.

29. The method according to claim 27, wherein cysteine endoprotease or the malt extract comprising cysteine endoprotease is added in a sufficient amount so that said fermented cereal-based beverage reaches up to 1°P on the Plato gravity scale 8 days after the start of the fermentation; and wherein addition of cysteine endoprotease or a malt extract comprising cysteine endoprotease reduces the cloudiness of the fermented cereal-based beverage by at least 65 EBC units when turbidity is measured at $-8°$ C. as compared to an identical fermented cereal-based beverage that has not undergone said treatment.

30. The method according to claim 29, wherein turbidity is measured using the Chapon test.

31. The method according to claim 27, wherein the malt extract is a processed malt extract that is obtained by recovery and centrifugation filtration of a crude malt extract.

32. The method according to claim 31, wherein the processed malt extract is treated by differential precipitation with ammonium sulphate.

33. The method according to claim 27, wherein the malt extract is a concentrated malt extract.

34. The method according to claim 27, wherein the fermented cereal-based beverage is beer.

35. The method according to claim 34, wherein the beer is selected from the group consisting of low-fermentation beers, high fermentation beers, beers of single, double or triple fermentation, beers with spontaneous fermentation, beers with mixed fermentation, beers prepared with additives, and beers with a range of alcohol levels from 0 to 10%.

36. The method according to claim 27, wherein cysteine endoprotease is selected from the group consisting of cysteine endoprotease A and cysteine endoprotease B of malt.

37. The method according to claim 27 wherein the malt extract is obtained from green malt or dry malt.

38. The method according to claim 27 wherein the malt extract is made from wheat or barley malt.

\* \* \* \* \*